(12) United States Patent
Bublewitz et al.

(10) Patent No.: US 7,790,781 B2
(45) Date of Patent: Sep. 7, 2010

(54) CONDENSATION-CROSSLINKABLE DENTAL MATERIAL HARDENING TO DIMENSIONALLY STABLE CASTS

(75) Inventors: Alexander Bublewitz, Herborn (DE); Jens-Peter Reber, Meinerzhagen (DE)

(73) Assignee: Kettenbach GmbH & Co. KG, Eschenburg (DE)

(*) Notice: Subject to any disclaimer, the term of this patent is extended or adjusted under 35 U.S.C. 154(b) by 1006 days.

(21) Appl. No.: 11/480,245

(22) Filed: Jun. 30, 2006

(65) Prior Publication Data
US 2007/0004821 A1 Jan. 4, 2007

(30) Foreign Application Priority Data
Jul. 1, 2005 (DE) ........................ 10 2005 031 201

(51) Int. Cl.
*A61K 6/10* (2006.01)
*C08L 83/04* (2006.01)
*A61C 9/00* (2006.01)

(52) U.S. Cl. .................... 523/109; 524/588; 528/44; 433/214

(58) Field of Classification Search ................ 523/109; 524/588; 528/44
See application file for complete search history.

(56) References Cited

U.S. PATENT DOCUMENTS

| | | | |
|---|---|---|---|
| 3,082,527 A | 3/1963 | Nitzsche et al. | |
| 3,127,363 A | 3/1964 | Nitzsche et al. | |
| 3,825,618 A | 7/1974 | Pepe | |
| 4,160,778 A | 7/1979 | Hildon et al. | |
| 4,174,338 A | 11/1979 | Goller et al. | |
| 4,362,885 A | 12/1982 | Panster et al. | |
| 4,375,549 A | 3/1983 | Renga | |
| 4,798,878 A | 1/1989 | Brinkmann et al. | |
| 4,906,707 A | 3/1990 | Yukimoto et al. | |
| 5,086,148 A | 2/1992 | Jochum et al. | |
| 5,118,290 A | 6/1992 | Müller | |
| 5,249,862 A | 10/1993 | Herold et al. | |
| 5,286,105 A | 2/1994 | Herold et al. | |
| 5,332,122 A | 7/1994 | Herold et al. | |
| 5,623,030 A * | 4/1997 | Tsumura et al. ............. | 525/478 |
| 5,739,245 A | 4/1998 | Lubbers et al. | |
| 5,916,981 A | 6/1999 | Cifuentes et al. | |
| 5,925,723 A | 7/1999 | Friebe et al. | |
| 6,077,696 A * | 6/2000 | Khosla et al. ............... | 435/135 |
| 6,077,896 A | 6/2000 | Yano et al. | |
| 6,124,235 A | 9/2000 | Letoffe et al. | |
| 6,129,244 A | 10/2000 | Hörth | |
| 6,218,461 B1 * | 4/2001 | Schwabe et al. ............. | 524/588 |
| 6,310,170 B1 | 10/2001 | Johnston et al. | |
| 6,503,994 B1 | 1/2003 | Nehren et al. | |
| 6,599,974 B1 | 7/2003 | Bublewitz et al. | |
| 6,884,852 B1 | 4/2005 | Klauck et al. | |
| 7,132,462 B2 * | 11/2006 | Lehmann et al. ............. | 523/109 |
| 2002/0086942 A1 | 7/2002 | Fujita et al. | |
| 2002/0156149 A1 | 10/2002 | Schaub et al. | |
| 2002/0156186 A1 | 10/2002 | Bublewitz et al. | |
| 2003/0083399 A1 | 5/2003 | Schaub et al. | |
| 2003/0158275 A1 | 8/2003 | McClelland et al. | |
| 2004/0042960 A1 | 3/2004 | Frey et al. | |
| 2004/0048998 A1 | 3/2004 | Klein et al. | |
| 2004/0146713 A1 | 7/2004 | Schaub et al. | |
| 2004/0181025 A1 | 9/2004 | Schindler | |
| 2005/0250871 A1 | 11/2005 | Bublewitz et al. | |
| 2005/0260401 A1 | 11/2005 | Bachon et al. | |

FOREIGN PATENT DOCUMENTS

| | | |
|---|---|---|
| DE | 11 63 021 | 2/1964 |
| DE | 19 59 842 | 9/1970 |
| DE | 26 44 193 | 4/1978 |
| DE | 44 39 769 | 5/1996 |
| DE | 100 61 195 | 6/2002 |
| DE | 101 04 079 | 8/2002 |
| DE | 101 39 132 | 2/2003 |
| EP | 0 269 819 | 6/1988 |
| EP | 0 170 865 | 7/1989 |
| EP | 0 372 561 | 6/1990 |
| EP | 0 269 819 | 12/1993 |
| EP | 0 492 413 | 11/1994 |
| EP | 0 492 412 | 3/1995 |
| EP | 0 723 807 | 7/1996 |
| EP | 0 748 621 A2 | 12/1996 |
| EP | 0 950 908 | 10/1999 |
| EP | 0 541 972 | 9/2000 |
| EP | 1 081 191 | 3/2001 |
| EP | 1 226 808 | 7/2002 |
| EP | 1 402 873 A1 | 3/2004 |
| WO | WO 98/44860 | 10/1998 |
| WO | WO 99/18912 | 4/1999 |
| WO | WO 99/48942 | 9/1999 |
| WO | WO 01/12237 | 2/2001 |
| WO | WO 02/08323 | 1/2002 |
| WO | WO 02/45661 | 6/2002 |
| WO | WO 2005/077321 A1 | 8/2005 |

OTHER PUBLICATIONS

Schriftenreihe Pigmente Degussa Kieselsäuren [Publication Series Pigments Degussa Silicas], No. 12, p. 5, as well as No. 13, p. 3.

(Continued)

*Primary Examiner*—Tae H Yoon
(74) *Attorney, Agent, or Firm*—Collard & Roe, P.C.

(57) ABSTRACT

Condensation-crosslinked dental materials based on alkoxysilyl-functional and/or hydroxysilyl-functional polyethers are useful in dentistry for taking tooth impressions, bite registration, denture rebasing, or as temporary and permanent dental cement, temporary closure material, or dental prosthodontic material. The dental material has a composition containing at least one alkoxysilyl-functional and/or hydroxysilyl-functional polyether a), at least one catalyst b), and optionally water c) and at least one acidic compound d) that has a water solubility (20° C.) of no more than 150 g/l.

14 Claims, 1 Drawing Sheet

OTHER PUBLICATIONS

Ullmann's Encyclopedia of Industrial Chemistry, vol. 21, p. 523.
ZM 93 (Zahnmedizin) (2003) No. 15, p. 32.
Source: http://www.cem.msu.edu/~reusch/VirtualText/suppmnt2. htm Molecular Structure and Acidity, pp. 1-13.
Source: http://ww.tgs-chemie.de/pks-wert.htm.
Source: Y. Chiang, E.B. Whipple, J. Am. Chem. Soc., 1963, vol. 85 2763-2767.
Source: http://www.zirchrom.com/organic.htm, Dissociation Constants of Organic Acids and Bases, pp. 1-14.
Source: W.C. Davies, H.W. Addis, J. Chem. Soc., 1937, 1622-1629.
Extended European Search Report and English translation of same.

* cited by examiner

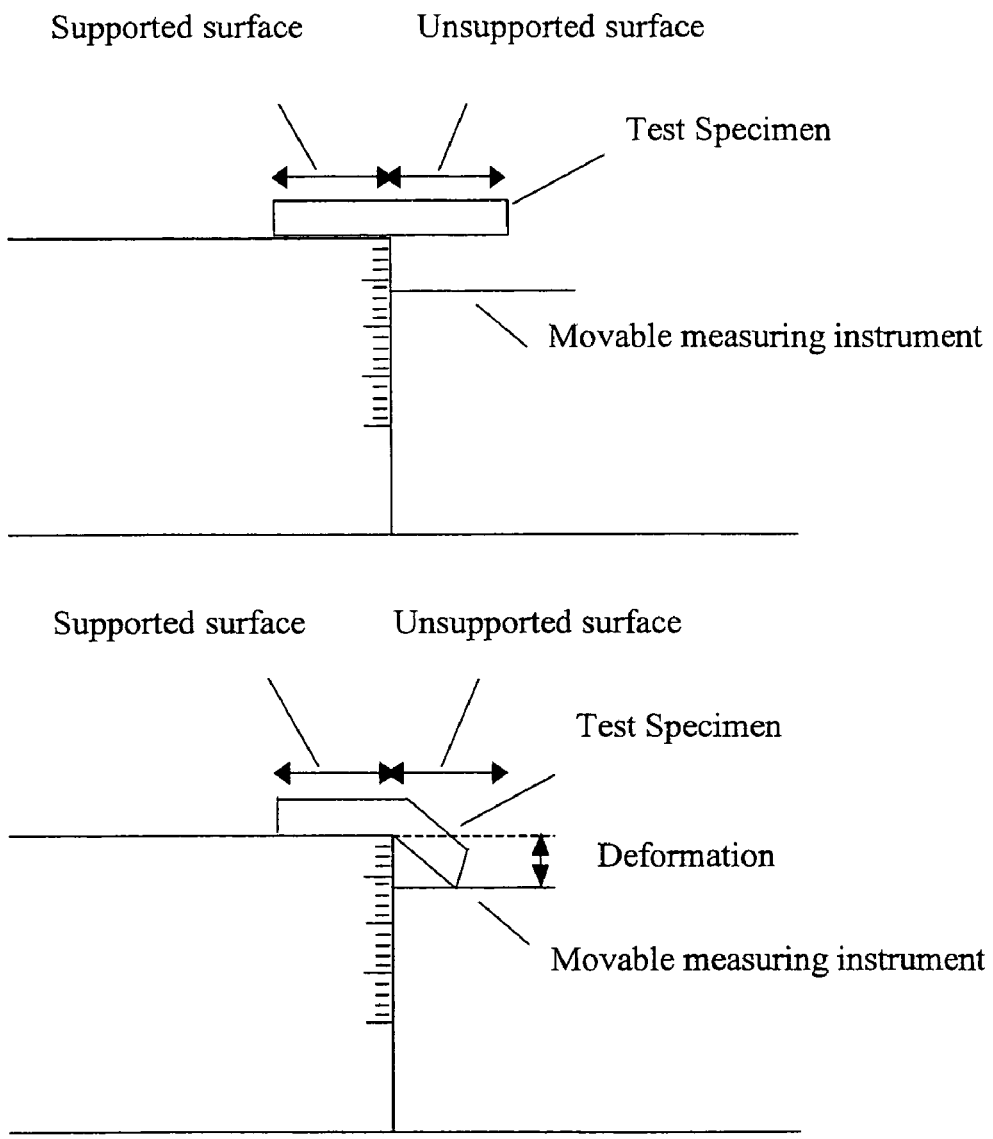

CONDENSATION-CROSSLINKABLE DENTAL MATERIAL HARDENING TO DIMENSIONALLY STABLE CASTS

CROSS REFERENCE TO RELATED APPLICATIONS

Applicants claim priority under 35 U.S.C. §119 of German Application No. 10 2005 031 201.2 filed on Jul. 1, 2005.

BACKGROUND OF THE INVENTION

1. Field of the Invention

This invention relates to condensation-crosslinkable dental materials, particularly condensation-crosslinkable two-component dental impression materials based on alkoxysilyl-functional and/or hydroxysilyl-functional polyethers, which are especially suitable for taking impressions. Such materials are used in dentistry, for example for taking tooth impressions, bite registration, denture rebasing, as temporary and permanent dental cement, temporary closure material, or dental prosthodontic material.

2. The Prior Art

Known condensation-crosslinking dental materials ordinarily contain hydroxy-functional polymers with a silicone backbone that harden in the presence of tin compounds as catalysts, alkoxysilanes and/or silicate esters as crosslinkers, and water. Of course, such materials are relatively hydrophobic because of the silicone backbone of the polymers, so that substantial proportions of surfactants have to be added to them to reduce surface tension and to establish the necessary wettability. Another drawback of these compositions is the use of toxicologically objectionable organic tin compounds as catalysts.

Alternatively to these, two-component dental materials are known that contain polymers having terminal alkoxysilyl groups with a hydrophilic polyether backbone, which have adequately hydrophilic properties for wetting the moist dental substance. These materials usually consist of a base component containing an alkoxysilyl-functional and/or hydroxysilyl-functional polyether with an average molecular weight of 800 to 20,000 g/mole, which may also have synthetically derived urea and/or urethane groups, fillers and optionally other additives, and a catalyst component that contains an organic and/or inorganic acid as catalyst in addition to fillers and optionally other auxiliaries. However, such materials, which are disclosed by European Patent Nos. EP 0 269 819 B1 and EP 1 226 808 A2, for example, have unsatisfactory properties for use because of the acid catalysis.

For this reason, base-catalyzed or salt-catalyzed hardening materials based on alkoxysilyl-functional polyethers have already been proposed. In International Publication No. WO 99/48942, organometallic compounds such as iron or tin compounds, for example tin (II) octanoate, or tertiary amines such as triethylamine are to be used as catalysts to crosslink polyurethanes that have polyether groups to be used as cements or sealants. However, the hardened vulcanizates/casts from these dental materials tend to lose their original shape by reversal of the crosslinking reaction (back-cleavage) after storage for some time at room temperature, and especially when stored at elevated temperature (e.g. 60° C.), and in extreme cases they tend to melt down with decomposition. Because of this, they are useless as a dental impression material since the finished impression may often be processed further to make a dental pattern only some time after taking the impression, or the impression has to be used again after a lengthy period of time (sometimes repeatedly) to make a dental pattern. Malformed or melted impressions then distort the dental pattern and lead to a useless dental prosthesis.

SUMMARY OF THE INVENTION

It is therefore an object of the invention to provide a base- or salt-catalyzed hydrophilic, condensation-crosslinkable dental impression material based on alkoxysilyl polyethers and/or hydroxysilyl polyethers that shows no back-cleavage, is dimensionally stable, and meets all the requirements for a dental material, after it is hardened and also after lengthy storage, especially lengthy storage at elevated temperatures.

This object is achieved pursuant to the invention by a condensation-crosslinkable dental material having a composition containing at least one alkoxysilyl-functional and/or hydroxysilyl-functional polyether a), at least one catalyst b), and optionally water c), with the at least one catalyst b) being selected from the group consisting of bases, salts, and any combinations thereof. The dental material also contains at least one acidic compound d) that has a water solubility (20° C.) of no more than 150 g/l.

It was found surprisingly in the course of this invention that reversal of the crosslinking reaction and/or back-cleavage as it necessarily occurs with base- and salt-catalyzed materials disclosed by the state of the art because the condensation reaction catalyzed by the free bases or by the salts is reversible and the catalysts are still present and active after the crosslinking reaction in the hardened state and therefore catalyze a back-reaction with cleavage of the previously formed Si—O—Si bond, can be reliably prevented by adding an acidic compound with water solubility no greater than 150 g/l measured at 20° C. to a base- or salt-catalyzed hardening dental material based on alkoxysilyl-functional and/or hydroxysilyl-functional polyethers. Therefore, the dental materials pursuant to the invention after hardening show high dimensional stability even after storage for months—including at elevated temperatures—while retaining the basic requirements for a dental impression material, for example storage stability of the individual components for a period of at least 12 months, adequate processing time, shortest possible setting time, toxicological harmlessness, and all other specifications as found in ISO 4823 (August 2001). In addition, it has been shown that despite the addition of the acidic compound pursuant to the invention to a base- or salt-catalyzed hardening dental material based on alkoxysilyl-functional and/or hydroxysilyl-functional polyethers, no spontaneous acceleration or slowing of the hardening reaction occurs. This was unexpected especially since acids are known to catalyze the hardening of alkoxysilyl- and hydroxysilyl-polyethers, which would lead one to expect acceleration of the hardening reaction in an acid-catalyzed system, and that alkoxysilyl-polyether mixtures containing bases and/or salts as catalyst could enter into a neutralization reaction with acidic compounds, which would necessarily slow down the hardening. According to the discoveries of this invention, premature acid-catalyzed hardening and a neutralization reaction are prevented by the low solubility of the acidic compound used pursuant to the invention.

According to the invention, the dental materials can be formulated as either a single-component or a two-component material. While the formulation of single-component dental materials has to be as absolutely anhydrous as possible, to prevent reaction of the alkoxysilyl-functional and/or hydroxysilyl-functional polyether during storage, and the reaction of the alkoxysilyl-functional and/or hydroxysilyl-functional polyether is initiated by oral moisture after application of the materials to the object to be modeled, it is preferred to add water to the catalyst component of the two-component dental material pursuant to the invention.

The two-component dental materials pursuant to the invention are preferably formulated so that Base Component A contains at least one alkoxysilyl-functional and/or hydroxysilyl-functional polyether, and the Catalyst Component B contains at least one catalyst selected from among the group consisting of bases, salts, and arbitrary combinations thereof, and water, with Component A also containing at least one acidic compound with a water solubility (20° C.) no greater than 150 g/l.

Basically, the dental material pursuant to the invention, in addition to the catalyst selected from among the group consisting of bases, salts, and arbitrary combinations thereof, can also contain any kind of acidic compound d) as long as the water solubility of the acidic compound d) and/or of all added acidic compounds d) measured at 20° C. amounts to no more than 150 g/l. Particularly good results are obtained in particular when the at least one acidic compound d), and with particular preference all of the added acidic compounds d) is/are selected from the group consisting of organic acids, inorganic acids, inorganic acid anhydrides, organic acid anhydrides, and arbitrary combinations thereof.

In a refinement of the invention, at least one acidic compound d) with a water solubility (20° C.) of no more than 50 g/l, and preferably no more than 1 g/l, and with special preference no more than 0.5 g/l, is used. If the dental material has a plurality of acidic compounds d), all of them preferably satisfy the aforementioned criteria.

According to another preferred embodiment of this invention, the at least one acidic compound d) has a polyether solubility (20° C.) of no more than 2 g/l, and preferably no more than 1 g/l, and very particularly no more than 0.5 g/l. Polyether solubility in the context of this invention means the solubility of a compound at 20° C. in a polyether with the following formula:

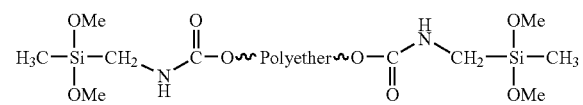

Good results are obtained particularly when at least one acidic compound d) with a $pK_a$ between 1.0 and 6.5 measured in water (20° C.) is added to the dental material, with acidic compounds d) with a $pK_a$ between 1.3 and 5.0 being preferred, and especially those with a $pK_a$ between 1.5 and 4.3. If polyfunctional acids are used, it is sufficient for at least one of the $pK_a$ values, preferably the $pK_{a1}$ of the polyfunctional acid used, to lie within the aforementioned ranges. When acid anhydrides are used, the $pK_a$ of the acid underlying the anhydride is what matters; in the case of succinic acid, for example, this is the $pK_a$ of succinic acid.

Examples of suitable compounds d) that satisfy the aforementioned criteria and that are therefore preferably used are barbituric acid, succinic anhydride, and especially ethylenediaminetetraacetic acid (CAS No. 60-00-4), derivatives of ethylenediaminetetraacetic acid, mono-, di-, and tri-alkali metal salts of ethylenediaminetetraacetic acid, and mono-, di-, and tri-alkaline earth metal salts of ethylenediaminetetraacetic acid. The dental material preferably contains only one acidic compound d), specifically one selected from the group consisting of ethylenediaminetetraacetic acid, mono-, di-, and tri-alkali metal salts of ethylenediaminetetraacetic acid, and mono-, di-, and tri-alkaline earth metal salts of ethylenediaminetetraacetic acid.

BRIEF DESCRIPTION OF THE DRAWINGS

The sole FIGURE shows the determination of the sag of a test specimen under the force of gravity, the measurement taken by placing T-square on the bottom of the test specimen and reading on the scale.

According to another particular embodiment of this invention, the dental material contains 0.001 to 10 wt. % of at least one acidic compound d) based on the total mixture, with special preference 0.01 to 5 wt. %, with very special preference 0.1 to 2 wt. %, and with highest preference 0.2 to 1.5 wt. %. Especially good results are obtained in particular when the dental material contains only one acidic compound d) in the aforementioned ranges of quantity.

In further refinement of the concept of the invention, it is proposed to formulate the dental material so that it is dimensionally stable after hardening and subsequent storage at room temperature for at least 1 month, preferably at least 3 months, and with special preference for at least 6 months, and/or after storage between 40° C. and 60° C. for at least 1 week, preferably at least 2 weeks, and with special preference at least 3 weeks.

To test the dimensional stability in the context of this invention, rectangular test specimens of the hardened dental impression material consisting of components A and B with dimensions of 40×12.5×5 mm and with a Shore A hardness in the range of 50-70 are fastened on one face to a slide carrier so that one half, 20×12.5×5 mm, extends unsupported beyond the slide carrier, and is exposed to the gravitational force of its own weight. The supported and projecting areas of the test specimen are chosen so that no spontaneous deformation occurs from the force of gravity alone. Supporting on half of the test specimen surface as indicated here proved practical for test specimens with a Shore hardness of 50-70. Other test specimens with a Shore hardness of 30-50 should be applied with a larger support surface of 70% of 40 mm, corresponding to 28×12.5×5 mm, and correspondingly smaller projecting surface of 30% of 40 mm, corresponding to 12×12.5×5 mm. At given time intervals, the vertical sag l (deformation) of the test specimen stored at 23° C. or 60° C., for example, is measured relative to its original starting position.

Dimensionally stable in the context of the invention means test specimens whose deformation l after storage for 1 week at 60° C. or for 12 weeks at room temperature is less than 1 mm, preferably less than 0.5 mm, with special preference less than 0.25 mm, and with very particular preference less than 0.1 mm. In addition, the recovery after deformation after storage for 1 week at 60° C. or for 12 weeks at room temperature should differ from the starting value, measured according to ISO 4823 (August 2001) Test Point 9.7, by less than 0.4, preferably less than 0.3, with special preference less than 0.2, and with very particular preference less than 0.1. The Shore A hardness for a dimensionally stable test specimen after storage for 1 week at 60° C. or for 12 weeks at room temperature should decrease from the starting value according to DIN 53505 (August 2000) by less than 4, preferably by less than 3, with special preference by less than 2, and with very particular preference by less than 1.

According to another preferred embodiment of this invention, the dental material is formulated as two-component dental material, with the base component A containing the alkoxysilyl- and/or hydroxysilyl-polyether a) and the at least one acidic compound d) being stable in storage at room temperature for at least 6 months, preferably at least 12 months, with special preference at least 18 months, and most preferably at least 24 months, and/or being stable at a storage temperature between 40° C. and 60° C. for at least 1 week, preferably at least 2 weeks, with special preference at least 3 weeks, and most preferably at least 4 weeks.

Kinetic storage stability in the context of this invention means that Component A with the addition of the acidic compound d) shows no premature crosslinking during storage for 6 months, preferably 12 months, and with special preference 24 months. Rheological tests of the loss modulus and of the storage modulus provide evidence of any premature crosslinking during the storage time. For kinetic storage stability, the storage modulus must not exceed a definite limit.

Storage stability in the context of this invention means that the base component A with the addition of acidic compound retains its rheological properties, in other words that no change of viscosity toward higher or low viscosities/consistencies occurs, with the consistency measurement preferably being made with 0.5 ml, 500 g, and 15 seconds following ISO 4823 (August 2001), Test Point 9.2, with a tolerance of ±4 mm, preferably ±3 mm, with special preference ±2 mm, and most preferably ±1 mm.

The base component A with the addition of acidic compound d) is also preferably stable in storage with respect to reaction kinetics/hardening. In other words, the processing and hardening times originally set after mixing Components A and B are constant within certain tolerances, with the processing time being determined with a McCabe rheometer and the setting time being determined with a Brabender Cycloviscograph E. The tolerances for the processing and/or hardening times preferably lie within ±45 seconds, with special preference ±30 seconds, and most preferably ±15 seconds.

The spontaneous setting retardation of the dental impression material caused by the addition of at least one acidic compound d) after mixing Components A and B should also be within certain tolerances, with the difference between the setting times with and without the addition of acidic (neutralizing) agents preferably being ±1.0 minute, with special preference ±45 seconds, very preferably ±30 seconds, and most preferably ±15 seconds.

In principle, all polyethers containing alkoxysilyl groups and/or hydroxysilyl groups can be used as alkoxysilyl-functional and/or hydroxysilyl-functional polyethers a), wherein the polyether backbone can be linear and/or branched, and can be made up of polyethylene oxide, polypropylene oxide, polytetrahydrofuran, and/or their copolymers, for example, and these monomers can be arranged statistically, blockwise, or in tactic arrangement. Mono- or polyfunctional alcohols such as methanol, butanol, glycerin, trimethylolpropane, pentaerythritol, and sorbitol, for example, can be used as initiators for the polyethers and/or copolymers. For example, copolymers of polytetrahydrofuran with polyethylene oxide or of polyethylene oxide with polypropylene oxide can be used, with pure polypropylene oxide being especially preferred. Also preferred are polyethers with lateral alkyl groups, with every monomeric structural unit or at least every tenth unit carrying a lateral alkyl group. Suitable commercial products are Acclaim® 4200, Acclaim® 6320N, Acclaim® 12200, Acclaim® 8200, and Acclaim® 6300 from Bayer AG, Polyglycol P41/300 and Polyglycol P41/3000 (Clariant), as well as poly(ethylene glycol-ran-propylene glycol) (Aldrich). The polyethers a) preferably have a number average molecular weight of 500 to 25,000 g/mole, and with special preference 5,000 to 20,000 g/mole.

In addition to chain length (elasticity), the alkoxysilyl and/or hydroxysilyl functionalization (hardening kinetics), and the number of urethane/urea groups (viscosity, rheology), the hydrophilicity of the polyether, which is determined by the number, structure, and polarity of the monomeric repeat units of the polyether polymer, is a selection criterion for the polyethers suitable for the invention. On the one hand, the hydrophilicity for a dental impression material has to be high enough to assure good flow onto wet dental substance (low contact angle), but on the other hand the material must not be too hydrophilic, since otherwise water, moisture, or saliva would lead to swelling while taking the impression or during disinfection or while filling with plaster, and the necessary dimensional accuracy would no longer exist. Furthermore, the hydrophilicity of the polyether is also co-responsible along with other factors for the polyether solubility of the acidic compound d) to be used pursuant to the invention.

According to a preferred embodiment of this invention, the at least one alkoxysilyl-functional and/or hydroxysilyl-functional polyether has a content of polyether groups between 5 and 30 mmol/g, and with special preference between 10 and 25 mmol/g.

The alkoxysilyl and/or hydroxysilyl structural unit(s) is/are terminally positioned alkoxysilyl and/or hydroxysilyl structural units of the polyether a), based on the polymeric backbone, and fall under the general formula I

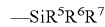

wherein $R^5$, $R^6$, and $R^7$ independently of one another are alkoxy, hydroxy, alkyl, aryl, aralkyl, or alkylaryl groups, hydrogen, or groups with the structure $—(O—C_xH_{2x})_y—OR$ with x=1 to 10, preferably x=1 to 6, and y=1 to 100, preferably y=2 to 6, with special preference y=2 to 4, and with particular preference y=3, and R=H or alkyl, with $R^5$, $R^6$, and $R^7$ independently of one another preferably being butoxy, propoxy, ethoxy, methoxy, hexyl, pentyl, butyl, propyl, ethyl, or methyl groups, with special preference hydroxy, ethoxy, methoxy, ethyl, or methyl groups, provided that at least one of the aforementioned residues, preferably two or all three residues, are alkoxy and/or hydroxy groups.

In a refinement of the concept of the invention, the at least one polyether a) has an alkoxy and/or hydroxy group content of 0.02 to 12 mmol/g, with special preference 0.04 to 6, and most preferably 0.04 to 3 mmol/g.

The condensation kinetics and with it the processing and setting time of the dental material can be set by the nature and number of alkoxy and/or hydroxy groups per silicon atom. These parameters are preferably chosen so that the processing time is 30 seconds to 3 minutes, with special preference between 1 and 2.5 minutes, and most preferably between 1.5 and 2 minutes, and/or the maximum setting time in the patient's mouth (so-called oral residence time) is 15 minutes, with special preference 10 minutes, very preferably 7 minutes, and most preferably less than or equal to 6 minutes, as determined according to ISO 4823 (1992 Edition).

The at least one polyether a) (besides the terminal alkoxy and/or hydroxy groups and the polyether groups) has a third structural unit of alkylene spacers, each located on the terminal alkoxysilyl- and/or hydroxysilyl groups, which are preferably $C_1$-$C_6$ alkyl groups, with special preference $C_1$-$C_3$ alkyl groups, very preferably ethylene groups and/or methylene groups, and most preferably methylene groups.

In addition, the at least one polyether a) as a fourth structural unit can have 0 to 8 mmol/g, with special preference 0 to 4 mmol/g, with very great preference 0.02 to 2 mmol/g, and most preferably 0.1 to 0.4 mmol/g of urethane groups and/or 0 to 8 mmol/g, with special preference 0 to 2 mmol/g, with very great preference 0.02 to 2 mmol/g, and most preferably 0.1 to 0.4 mmol/g of urea groups. Especially when the at least one polyether a) has urea and/or urethane groups as a fourth structural unit, a methylene group is preferred as a spacer.

Hydrophilic two-component dental impression materials stable in storage are obtained by using such α-activated alkoxysilyl- and/or hydroxysilyl-polyethers, which crosslink surprisingly rapidly by a condensation reaction with a salt or base to be used as a catalyst. The overall content of urethane or urea groups per molecule should be kept as small as possible in order to minimize intermolecular interactions between the individual polyether chains, to keep the viscosity caused by the polyether additive as low as possible, which allows the addition of larger amounts of fillers in the dental materials and thus allows more freedom in formulation and more economical formulations.

It is advantageous to use polyethers that contain no urethane or urea groups within the polymer chain and that carry no more than one urethane or urea group at the most, and no more than one alkoxysilyl- and/or hydroxysilyl group at the most, and no more than one methylene spacer group at the most, at each end of the chain. The use of these polyethers leads to formulations with lower viscosity than the polyurethane-alkoxysilyl- and/or hydroxysilyl-polyethers used in the state of the art, so that more fillers can be added to the dental materials, which leads to a reduction of production costs.

According to another particular embodiment of this invention, the individual structural units of the at least one polyether a) are arranged as follows:

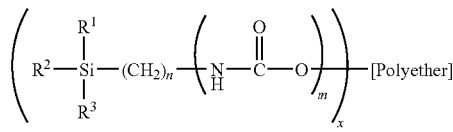

wherein $R^1$, $R^2$, and $R^3$ independently of one another are alkoxy, hydroxy, alkyl, aryl, aralkyl, alkylaryl groups, hydrogen, or groups with the structure —(O—$C_xH_{2x}$)$_y$—OR with x=1 to 10, preferably x=1 to 6, and y=1 to 100, preferably y=2 to 6, with special preference y=2 to 4, and with particular preference y=3, and R=H or alkyl, with $R^1$, $R^2$, and $R^3$ independently of one another preferably being butoxy, propoxy, ethoxy, methoxy, hexyl, pentyl, butyl, propyl, ethyl, or methyl groups, with special preference hydroxy, ethoxy, methoxy, ethyl, or methyl groups, provided that at least one of the aforementioned residues, preferably two or all three residues, are alkoxy and/or hydroxy groups, and x=1 to 6, preferably x=2 to 4, and with special preference x=2, n=1 to 6, preferably n=1 to 3, and with special preference n=1, and m=0 or 1, with special preference m=1, or

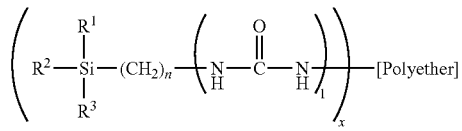

wherein $R^1$, $R^2$, and $R^3$ independently of one another are alkoxy, hydroxy, alkyl, aryl, aralkyl, alkylaryl groups, hydrogen, or groups with the structure —(O—$C_xH_{2x}$)$_y$—OR with x=1 to 10, preferably x=1 to 6, and y=1 to 100, preferably y=2 to 6, with special preference y=2 to 4, and with particular preference y=3, and R=H or alkyl, with $R^1$, $R^2$, and $R^3$ independently of one another preferably being butoxy, propoxy, ethoxy, methoxy, hexyl, pentyl, butyl, propyl, ethyl, or methyl groups, with special preference hydroxy, ethoxy, methoxy, ethyl, or methyl groups, provided that at least one of the aforementioned residues, preferably two or all three residues, are alkoxy and/or hydroxy groups, and x=1 to 6, preferably x=2 to 4, and with special preference x=2, n=1 to 6, preferably n=1 to 3, and with special preference n=1, and l=0 or 1, and with special preference l=1.

According to another preferred embodiment of this invention, the alkyl spacer in the aforementioned structural units is methylene (n=1).

The preparation of these alkoxysilyl-functional and/or hydroxysilyl-functional polyethers is known and is described, for example in German Patent No. DE 101 04 079 A1, European Patent No. EP 0 629 819 B1, German Patent No. DE 101 39 132, U.S. Pat. No. 4,906,707, European Patent No. EP 0 372 561 A1, European Patent No. EP 1 303 560 A1, and European Patent No. EP 0 170 865 B1, which are hereby incorporated by reference are part of the disclosure. Examples of commercially obtainable polyethers suitable in the context of this invention are MS Polymer S 203H, MS Polymer S 303H (Kaneka), Polymer XP ST55, ST50, ST51, ST53 (Hanse), SLM 414000 (Wacker), SLM 414001 (Wacker), Baycoll® XP 2458, and Desmoseal® XP 2447 (Bayer AG), with dimethoxy(methyl)silylmethylcarbamate-terminated polyether sold under the trade name SLM 414000:

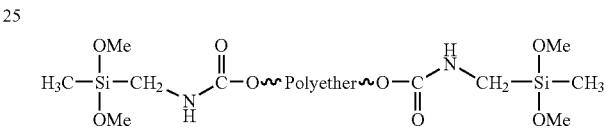

and dimethoxy(methyl)silylmethylurea-terminated polyether:

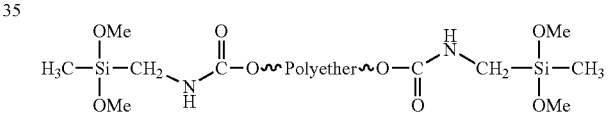

being particularly preferred.

Basically, the dental materials pursuant to the invention can contain all catalytically active free bases or salts as catalyst b).

According to a first particular embodiment of this invention, the dental material contains one or more free bases as catalyst b), with organic bases with a $pK_{BH+}$ value of at least 20 measured in acetonitrile being preferred.

Independently of formulation as a single-component or two-component material, the at least one base b) to be used as a catalyst according to the invention preferably has a $pK_{BH+}$ value of at least 21 measured in acetonitrile, with special preference of at least 22, and with very special preference of at least 23.

According to a sub-embodiment of the first particular embodiment of this invention, an organic base is used as catalyst b) that comprises at least one structural unit according to the general formula II

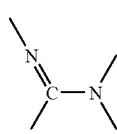

and/or according to the general formula III

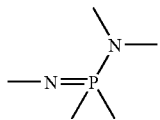

and/or according to the general formula IV

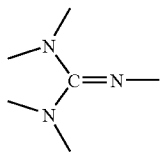

In particular, good results are obtained when the catalyst b) is at least one organic base selected from the group consisting of

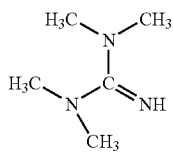

1,1,3,3-Tetramethylguanidine (TMG)

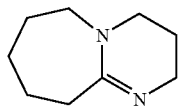

Diazabicyclo[5.4.0]undec-7-ene (DBU)

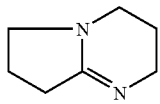

1,5-Diazabicyclo[4.3.0]non-5-ene (DBN)

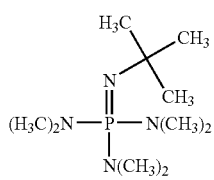

tert-Butylimino-tri(pyrrolidino)phosphorane

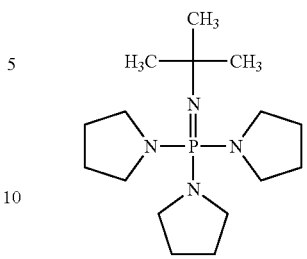

tert-Butylimino-tris(dimethylamino)phosphorane

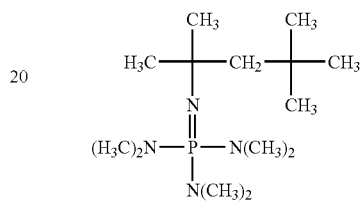

tert-Octylimino-tris(dimethylamino)phosphorane

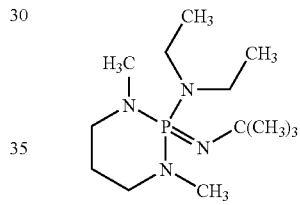

2-tert-Butylimino-2-diethylamino-1,3-dimethyl-perhydro-1,3,2-diazaphosphorine

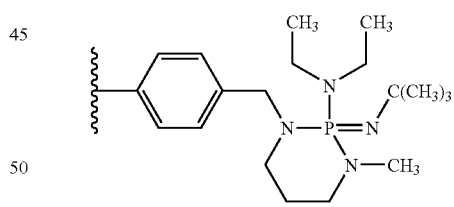

2-tert-Butylimino-2-diethylamino-1,3-dimethyl-perhydro-1,3,2-diazaphosphorine on polystyrene

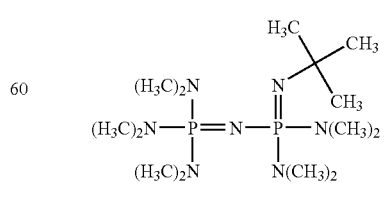

1-tert-Butyl-2,2,4,4,4-pentakis(diethylamino)-2$\lambda$5,4$\lambda$5-catenadi(phosphazene)

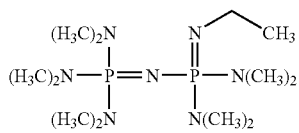

1-Ethyl-2,2,4,4,4-pentakis(diethylamino)-2λ5,4λ5-catenadi(phosphazene)

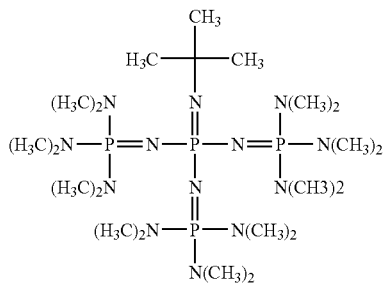

1-tert-Butyl-4,4,4-tris(dimethylamino)-2,2-bis[tris(dimethylamino)-phosphor-anylidenamino]-2λ⁵,4λ⁵-catenadi(phosphazene)

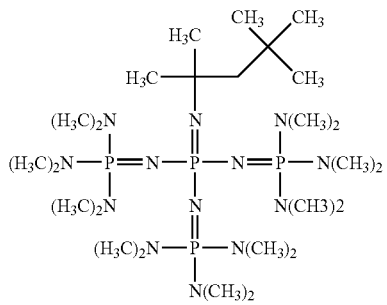

1-tert-Octyl-4,4,4-tris(dimethylamino)-2,2-bis[tris(dimethylamino)-phosphor-anylidenamino]-2λ⁵,4λ⁵-catenadi(phosphazene)

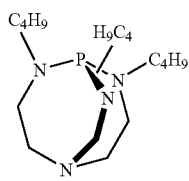

2,8,9-Triisobutyl-2,5,8,9-tetraaza-1-phosphabicyclo[3.3.3]undecane

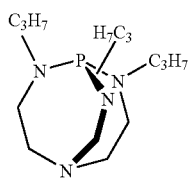

2,8,9-Triisopropyl-2,5,8,9-tetraaza-1-phosphabicyclo[3.3.3]undecane

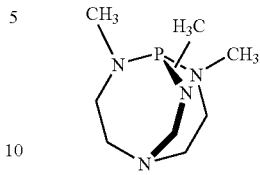

2,8,9-Trimethyl-2,5,8,9-tetraaza-1-phosphabicyclo[3.3.3]undecane

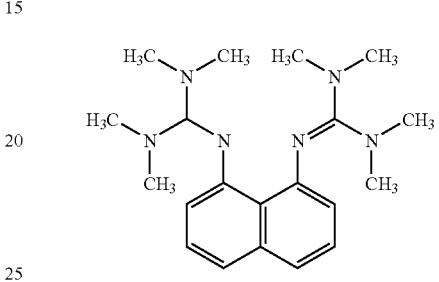

1,8-Bis(tetramethylguanidino)naphthalene (TMGN)

and 2-tert-butyl-1,1,3,3-tetramethylguanidine, 1,5,7-triazabicyclo(4.4.0)dec-5-ene, 7-methyl-1,5,7-triazabicyclo(4.4.0)dec-5-ene, 1,5-diazabicyclo[4.3.0]non-5-ene, and 3,3,6,9,9-pentamethyl-2,10-diazabicyclo-(4.4.0)dec-1-ene.

It is very highly preferred for the dental material pursuant to the invention to contain as catalyst b) at least one base selected from the group consisting of tert-butylimino-tri(pyrrolidino)phosphorane, 1-tert-butyl-2,2,4,4,4-pentakis (diethylamino)-2λ5,4λ5-catenadi(phosphazene), 1-tert-butyl-4,4,4-tris(dimethylamino)-2,2-bis[tris-(dimethylamino)-phosphoranylidenamino]-2λ⁵,4λ⁵-catenadi (phosphazene), tert-octylimino-tris(dimethylamino)phosphorane, 2,8,9-triisopropyl-2,5,8,9-tetraaza-1-phosphabicyclo[3.3.3]undecane, 1,5-diazabicyclo[4.3.0]non-5-ene, 1,1,3,3-tetramethylguanidine, diazabicyclo[5.4.0]undec-7-ene, 7-methyl-1,5,7-triazabicyclo(4.4.0)dec-5-ene, 2-tert-butyl-1,1,3,3-tetramethylguanidine, 1,5,7-triazabicyclo(4.4.0)dec-5-ene, and 1,8-bis(tetramethylguanidino)naphthalene.

In furthering the concept of the invention, the aforementioned organic bases used as catalyst b) according to the invention have alkoxysilyl groups. This causes the base to be bound into the polyether matrix after the dental material hardens, and it can no longer be leached out of the dental impression material.

According to the invention, the dental materials can contain as catalyst b) one or more of the aforementioned organic bases, in any desired combination with one another. The dental material preferably contains only one of the aforementioned organic bases as catalyst b). It is especially preferred for no other catalysts to be used besides the one or more organic bases to be used pursuant to the invention, particularly no organometallic metal salts, no amines with $pK_{BH+}$ <20, and no free acids.

As one skilled in the art knows, the amount of catalyst base depends in part on the solubility of the base in the polyether matrix used. The amount of catalyst base(s) based on the total dental material mixture is preferably 0.001 to 1 mmol/g, more preferably 0.001 to 0.5 mmol/g, very preferably 0.001 to 0.1 mmol/g, and most preferably 0.005 to 0.05 mmol/g. Of course the organic base or mixture of bases used as catalyst b) must have a minimum solubility in the polyether matrix used to be able to act catalytically at all.

To keep the amount of catalyst base used as small as possible, the base can be a base with sufficiently high solubility in the polyether material, i.e. with adequate catalytic activity, with the catalytic activity in the context of this invention being characterized by the hardening time determined by recovery after deformation determined according to ISO 4823 (1992 version). It is preferred to use a base that produces with polytetrahydrofuran, polyethylene glycol, and with special preference polypropylene glycol, and their mixtures and copolymers as polyether matrix, a hardening time of less than 30 min, preferably less than 15 min for a dental prosthodontic composition, and a hardening time of less than 15 min, preferably less than 10 min, with special preference less than 7 min, and most preferably less than or equal to 6 min for a dental impression composition.

According to a second particular embodiment of this invention, the dental material contains a salt as catalyst b) that is formed from at least one cation selected from the group consisting of complexes of alkali metal or ammonium cations with crown ethers and/or cryptands, tetraalkyl-, tetraaryl- trialkylaryl-, dialkyldiaryl-, monoalkyltriarylammonium cations, tetraalkyl-, tetraaryl-, trialkylaryl-, dialkyldiaryl-, monoalkyltriarylphosphonium cations, tetraalkyl-, tetraaryl- trialkylaryl-, dialkyldiaryl-, monoalkyltriarylarsonium cations, tetraalkyl-, tetraaryl- trialkylaryl-, dialkyldiaryl-, monoalkyltriarylstibonium cations, cations formed by protonation of a base with a $pK_{BH+}$ value of at least 20 measured in acetonitrile and any desired combinations thereof, and at least one anion of a saturated and/or unsaturated (cyclo)aliphatic carboxylic acid, with the carboxylic acid being a branched carboxylic acid with a length of the (cyclo)alkyl chain provided on the carboxyl group of at least 2 carbon atoms, or an unbranched carboxylic acid with a length of the (cyclo)alkyl chain provided on the carboxyl group of at least 4 carbon atoms.

According to one version of this embodiment, the catalyst b) used is at least one salt formed from at least one crown ether-alkali metal ion complex, crown ether-ammonium ion complex, cryptand-alkali metal ion complex, and/or cryptand-ammonium ion complex, and at least one anion of a saturated and/or unsaturated (cyclo)aliphatic carboxylic acid, with the carboxylic acid being a branched carboxylic acid with a length of the (cyclo)alkyl chain provided on the carboxyl group of at least 2 carbon atoms, or an unbranched carboxylic acid with a length of the (cyclo)alkyl chain provided on the carboxyl group of at least 4 carbon atoms.

In this embodiment, the cation of the catalyst salt used is a complex formed from one or more lithium, sodium, potassium, rubidium, cesium, and/or ammonium ions and one or more of the following crown ethers and/or cryptands:

15-Crown-5,18-crown-6, dibenzo-18-crown-6, dibenzo-21-crown-7, dibenzo-24-crown-8, dibenzo-30-crown-10, 1,4,10-trioxa-7,13-diazacyclopentadecane, 4,7,13,18-tetraoxa-1,10-diazabicyclo[8.5.5]eicosane, 1,4,10,13-tetraoxa-7,16-diazacyclooctadecane, 3,6,9,14-tetrathiabicyclo[9.2.1]tetradeca-11,13-diene, 1,4,7,10-tetrathiacyclododecane, 1,5,9,13-tetrathiacyclohexadecane-3,11-diol, 1,5,9-triazacyclododecane, 1,4,7-triazacyclononane, 1,4,7,10,13,16-hexamethyl-1,4,7,10,13,16-hexaazacyclooctadecane,

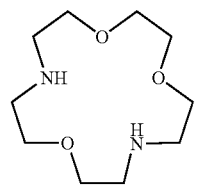

1,4,10-Trioxa-7,13-diaza-cyclopentadecane

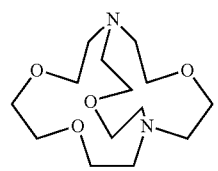

4,7,13,18-Tetraoxa-1,10-diazabicyclo[8.5.5]eicosane

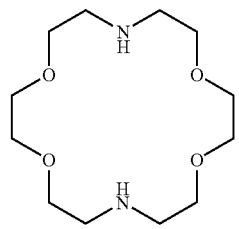

1,4,10,13-Tetraoxa-7,16-diazacyclooctadecane

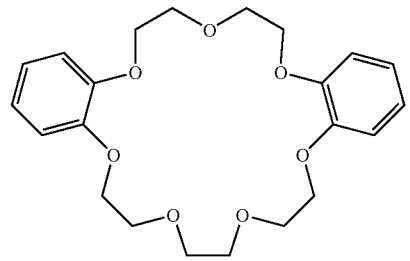

Dibenzo-21-crown-7

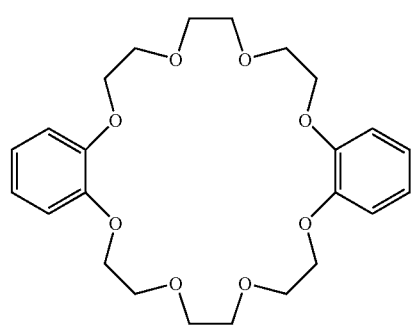

Dibenzo-24-crown-8

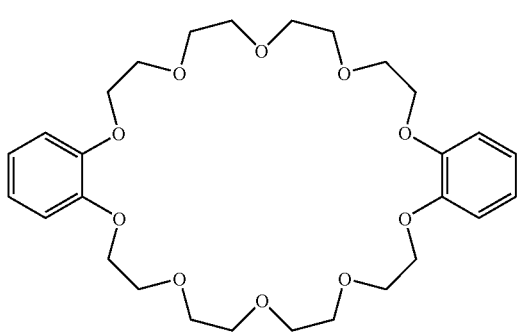

Dibenzo-30-crown-10

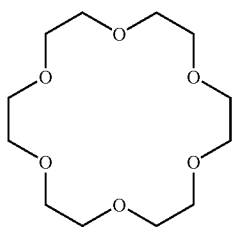

18-crown-6

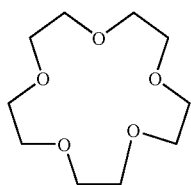

15-Crown-5

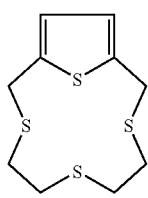

3,6,9,14-Tetrathiabicyclo[9.2.1]tetradeca-11,13-diene

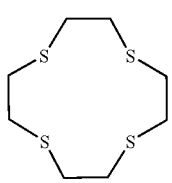

1,4,7,10-Tetrathiacyclododecane

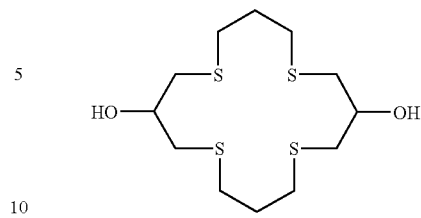

1,5,9,13-Tetrathiacyclohexadecane-3,11-diol

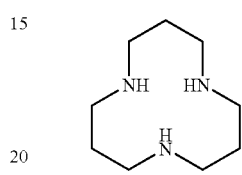

1,5,9-Triazacyclododecane

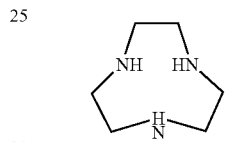

1,4,7-Triazacyclononane.

The catalyst salts to be used pursuant to the invention in this embodiment can be prepared by any method known to one skilled in the art, for example by the following reaction:

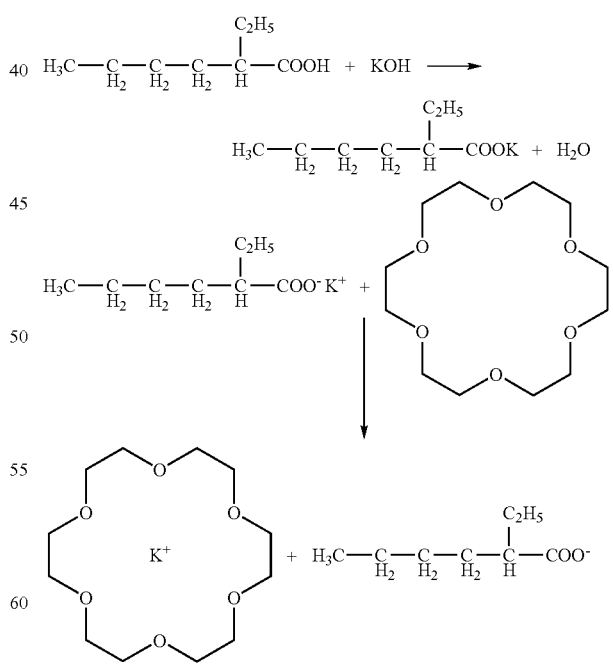

According to a second preferred sub-embodiment of the second particular embodiment of this invention, the catalyst b) used is at least one salt from at least one anion of a saturated and/or unsaturated (cyclo)aliphatic carboxylic acid, with the carboxylic acid being a branched carboxylic acid with a length of the (cyclo)alkyl chain provided on the carboxyl group of at least 2 carbon atoms, or an unbranched carboxylic acid with a length of the (cyclo)alkyl chain provided on the carboxyl group of at least 4 carbon atoms, and a tetraalkyl-, tetraaryl-, trialkylaryl-, dialkyldiaryl-, monoalkyltriarylammonium, tetraalkyl-, tetraaryl-, trialkylaryl-, dialkyldiaryl-, monoalkyltriarylphosphonium, tetraalkyl-, tetraaryl-, trialkylaryl-, dialkyldiaryl-, monoalkyltriarylarsonium, tetraalkyl-, tetraaryl-, trialkylaryl-, dialkyldiaryl-, and/or monoalkyltriarylstibonium cation. Examples of suitable cations for the catalyst salts to be used according to this embodiment are tetramethylammonium, tetraethylammonium, tetrapropylammonium, tetrabutylammonium, tetrapentylammonium, tetrahexylammonium, tetraheptylammonium, tetraoctylammonium, tetranonylammonium, tetradecylammonium, Tetramethylphosphonium, tetraethylphosphonium, tetrapropyl-phosphonium, tetrabutylphosphonium, tetrapentylphosphonium, tetrahexylphosphonium, tetraheptylphosphonium, tetraoctylphosphonium, tetranonylphosphonium, tetradecylphosphonium, tetramethylarsonium, tetraethylarsonium, tetrapropylarsonium, tetrabutylarsonium, tetrapentylarsonium, tetrahexylarsonium, tetraheptylarsonium, tetraoctylarsonium, tetranonylarsonium, tetradecylarsonium, tetramethylstibonium, tetraethylstibonium, tetrapropylstibonium, tetrabutylstibonium, tetrapentylstibonium, tetrahexylstibonium, tetraheptylstibonium, tetraoctylstibonium, tetranonylstibonium, tetradecylstibonium, lauryltrimethylammonium, myristyltrimethylammonium, cetyltrimethylammonium, stearyltrimethylammonium, lauralkonium, myristalkonium, cetalkonium, stearalkonium, cetylethyldimethylammonium, benzyltriethylammonium, and benzalkonium ions.

The salts of the aforementioned carboxylate anions and the alkyl- and/or aryl-substituted ammonium, phosphonium, arsonium, or stibonium ions according to this form of embodiment can be prepared by any method known to one skilled in the art, with the following synthesis having proved to be particularly suitable, for example:

cation formed by the protonation of a base with a $pK_{BH+}$ value of at least 20 measured in acetonitrile. Especially good results are obtained when the dental material contains as catalyst b) a salt formed from an aforementioned anion and a cation formed by protonation of a base with a $pK_{BH+}$ value of at least 21, with special preference 22, and very particularly preferably 23 measured in acetonitrile.

In furtherance of the concept of the invention, it is proposed in the third sub-embodiment of this invention to use as catalyst b) a salt formed from an anion of one of the aforementioned carboxylic acids and a protonated base, with the base having a structure that allows mesomeric stabilization of the positive charge after protonation of the base. Mesomeric stabilization in the context of this invention, in agreement with general textbook knowledge, means that at least two limiting structures can be drawn for the protonated base in which the positive charge is localized on different atoms, and that n-electrons are delocalized in the protonated base. Particularly preferred are catalyst salts formed from an anion of one of the aforementioned carboxylic acids and a protonated base in which the base has at least one structural unit according to one of the aforementioned general formulas II to IV. These structural units, after protonation of the base, lead to good mesomeric stabilization of the positive charge, which leads to stabilization of the protonated form.

Good results are produced for the third sub-embodiment of the second particular embodiment of this invention, especially when a protonated base is used as a cation that is selected from the group described for the first particular embodiment of this invention.

It is preferred for the base component of the salt according to this embodiment of this invention to be tert-butylimino-tri (pyrrolidino)phosphorane, 1-tert-butyl-2,2,4,4,4-pentakis(diethylamino)-2Λ5,4Λ5-catenadi(phosphazene), 1-tert-butyl-4,4,4-tris(dimethylamino)-2,2-bis[tris-(dimethylamino)-phosphoranylidenamino]-2Λ$^5$,4Λ$^5$-catenadi(phosphazene), tert-octylimino-tris(dimethylamino)phosphorane, 2,8,9-triisopropyl-2,5,8,9-tetraaza-1-phosphabicyclo[3.3.3]unde-

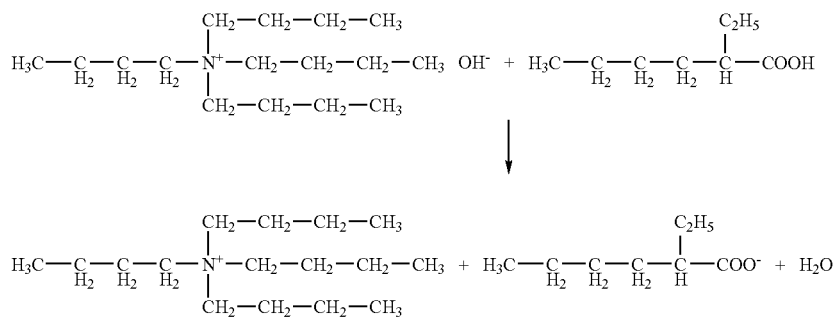

According to a third preferred sub-embodiment of the second particular embodiment of this invention, the catalyst b) used is at least one salt formed from at least one anion of a saturated and/or unsaturated (cyclo)aliphatic carboxylic acid, with the carboxylic acid being a branched carboxylic acid with a length of the (cyclo)alkyl chain provided on the carboxyl group of at least 2 carbon atoms, or an unbranched carboxylic acid with a length of the (cyclo)alkyl chain provided on the carboxyl group of at least 4 carbon atoms, and a cane, 1,5-diazabicyclo[4.3.0]non-5-ene, 1,1,3,3-tetramethylguanidine, diazabicyclo[5.4.0]undec-7-ene, 7-methyl-1,5,7-triazabicyclo(4.4.0)dec-5-ene, 2-tert-butyl-1,1,3,3-tetramethylguanidine, 1,5,7-triazabicyclo(4.4.0)dec-5-ene, and/or 1,8-bis(tetramethylguanidino)naphthalene.

The catalyst salt according to the third embodiment of this invention formed by acid-base reaction can be prepared by any method known to one skilled in the art, for example by the following reaction:

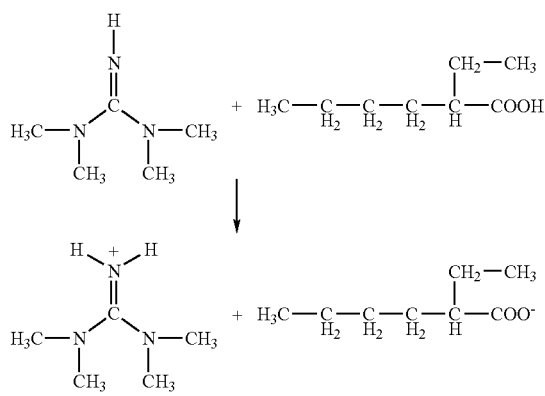

According to the invention, any salt formed from at least one of the aforementioned cations and at least one of the aforementioned carboxylate anions can be used. Preferred salts are ones in which the anion of the catalyst salt is an anion of a branched carboxylic acid with a length of the (cyclo)alkyl chain provided on the carboxyl group of at least 3 carbon atoms, with special preference 4, and with very special preference at least 5 carbon atoms, or of an unbranched carboxylic acid with a length of the (cyclo)alkyl chain provided on the carboxyl group of at least 5 carbon atoms. Also preferred are salts in which the anion is an anion of a saturated and/or unsaturated (cyclo)aliphatic monocarboxylic acid with a (cyclo)alkyl chain length as mentioned previously.

Especially good results are also produced in particular with salts comprising at least one aliphatic or cycloaliphatic carboxylate anion resulting from deprotonation with a (cyclo)alkyl chain that has at least one and preferably at least two branches. Preferably used as the anion of the at least one catalyst salt is an aliphatic or cycloaliphatic carboxylate anion that has at least one branch in the γ-position, with special preference at least one branch in the β-position, and with very great preference at least one branch in the α-position to the carboxyl group of the carboxylate anion. Likewise preferred are corresponding carboxylate anions in whose (cyclo)alkyl chain there is at least one branch in the γ-, β-, and/or α-position to the carboxylate anion.

In a refinement of the concept of the invention, especially for the third sub-embodiment, in which the cation of the catalyst salt is formed by protonation of a base, catalyst b) in the dental material can be at least one salt formed from one of the aforementioned cations and an anion of an acid selected from the group consisting of 2,2-dialkylalkanoic acid, 3,3-dialkylalkanoic acid, 4,4-dialkylalkanoic acid, 2,3-dialkylalkanoic acid, 2,4-dialkylalkanoic acid, 3,4-dialkylalkanoic acid, 2,2-dialkylalkenoic acid, 3,3-dialkylalkenoic acid, 4,4-dialkylalkenoic acid, 2,3-dialkylalkenoic acid, 2,4-dialkylalkenoic acid, 3,4-dialkylalkenoic acid, 2,2-dialkylalkynoic acid, 3,3-dialkylalkynoic acid, 4,4-dialkylalkynoic acid, 2,3-dialkylalkynoic acid, 2,4-dialkylalkynoic acid, 3,4-dialkylalkynoic acid, 2-monoalkylalkanoic acid, 3-monoalkylalkanoic acid, 4-monoalkylalkanoic acid, 2,2-dialkylhexanoic acid, preferably 2,2-dialkylnonanoic acid, 2,2-dimethyldecanoic acid, 2,2-diethyldecanoic acid, 2,2-dipropyldecanoic acid, 2,2-dibutyldecanoic acid, 2,2-dimethylnonanoic acid, 2,2-diethylnonanoic acid, 2,2-dipropylnonanoic acid, 2,2-dibutylnonanoic acid, 2,2-dimethyloctanoic acid, 2,2-diethyloctanoic acid, 2,2-dipropyloctanoic acid, 2,2-dibutyloctanoic acid, 2,2-dimethylheptanoic acid, 2,2-diethylheptanoic acid, 2,2-dipropylheptanoic acid, 2,2-dibutylheptanoic acid, 2,2-dimethylhexanoic acid, 2,2-diethylhexanoic acid, 2,2-dipropylhexanoic acid, 2,2-dibutylhexanoic acid, 2-butyloctanoic acid, 2-hexyldecanoic acid, 2-propylpentanoic acid, 1-methyl-1-cyclohexanecarboxylic acid, 2,2-dimethylbutyric acid, 2,2-dimethylvaleric acid, 3,5,5,-trimethylhexanoic acid, 2-ethylhexanoic acid, decanoic acid, octanoic acid, hexanoic acid, and enanthic acid.

According to another preferred embodiment, the dental material is formulated as a two-component system and contains as catalyst b) at least one salt of diazabicyclo[5.4.0]undec-7-ene, diazabicyclo[4.3.0]non-5-ene, and/or 1,1,3,3-tetramethylguanidine with 2-alkylalkanoic acid, in particular 2-alkylhexanoic acid, 2-ethylhexanoic acid, 2,2-dialkylalkanoic acid, 2,2-dialkylhexanoic acid, 2,2-dialkylnonanoic acid, 2,2-dimethylhexanoic acid, 2,2-diethylhexanoic acid, 2,2-dimethylnonanoic acid, 2,2-diethylnonanoic acid, and/or 2-propylpentanoic acid.

In a refinement of the concept of the invention, the cations and/or carboxylate anions provided in the catalyst salts to be used pursuant to the invention have alkoxysilyl groups. This causes the catalyst salt to be bound into the polyether matrix after the hardening of the dental material, and to be unable any longer to be leached out of the dental impression material.

According to the invention, the dental materials can contain as catalyst b) one or more of the aforementioned salts, in any desired combination with one another. The dental material preferably contains only one of the aforementioned salts as catalyst; it is especially preferred to use no other catalysts besides the one or more salts to be used pursuant to the invention, particularly no organometallic metal salts, tertiary amines, or free acids.

In the dental material pursuant to the invention, it is preferred to use a catalyst salt b) with a pH measured in water (Ampuwa, pH 5.8) between 7 and 11, and with particular preference between 7 and 9.

One skilled in the art knows that the amount of catalyst salt to be used depends in part on the solubility of the salt in the polyether matrix used. The amount of catalyst salt to be used, based on the total dental material mixture, is preferably 0.001 to 1 mmol/g, more preferably 0.001 to 0.5 mmol/g, very preferably 0.001 to 0.1 mmol/g, and most preferably 0.005 to 0.05 mmol/g. Of course the catalyst salt used must have a minimum solubility in the polyether matrix used to be able to act catalytically at all.

To keep the amount of catalyst salt to be used as small as possible, it is proposed in a refinement of the concept of the invention to use in the dental material a catalyst salt with sufficiently high solubility in the polyether material, i.e. with adequate catalytic activity, with the catalytic activity being determined as described in connection with the first particular embodiment of this invention.

According to a third particular embodiment of this invention, the dental material contains as catalyst b) a salt that is formed from a weak organic base with a $pK_{BH+}$ between −1 and 7 measured in water, and at least one strong acid with a $pK_a$ of less than 2 measured in water.

According to a version of the third particular embodiment of this invention, the at least one catalyst is a salt that is formed from a weak organic base with a $pK_{BH+}$ between −1 and 7 measured in water, and at least one strong acid with a $pK_a$ of less than 2 measured in water, with the acid having a structure that permits mesomeric stabilization of the negative charge after deprotonation of the acid.

Regardless of whether the dental material pursuant to the invention is formulated as a single-component system or a two-component system, the catalyst salt used is preferably formed from at least one acid with a $pK_a$ of less than 1 measured in water, and with special preference of less than or equal to 0.7, and/or at least one base with a $pK_{BH+}$ between 1 and 7 measured in water, with special preference between 2 and 6, and with very special preference between 3 and 6.

According to another version of the third particular embodiment of this invention, the at least one catalyst salt is formed from an acid selected from the group consisting of p-toluenesulfonic acid, fluorosulfonic acid, trifluoromethanesulfonic acid, fluorosulfuric acid, 4-sulfophthalic acid, trichloroacetic acid, trifluoroacetic acid, benzenesulfonic acid, and combinations thereof, and/or a base selected from the group consisting of pyrrole derivatives, dimethylaniline, pyridine, 2,4,6,N,N-pentamethylaniline, N,N-dimethylaniline, phenetidine, acridine, phenanthridine, quinoline, isoquinoline, 2-amino-4,6-dimethylpyrazine, 4,6-dimethylpyridinamine, 3-methylpyridine (3-picoline), 4-phenylpyridine, 4-vinylpyridine, pyridazine, 2-ethylpyridine, 2-butylpyridine, 1,7-phenanthroline, 2-aminopyrimidine, 2-isopropylpyridine, 2-vinylpyridine, 2-N,N-dimethylaminopyridine, quinazoline, 4-chloropyridine, phenazine, 4-acetylpyridine, methyl nicotinate, 3-benzoylpyridine, 2,2'-bipyridine, 2-phenylpyridine, 2-tert-butylpyridine, pyrimidine, 3-iodopyridine, 3-fluoropyridine, 3-chloropyridine, 3-bromopyridine, pyrazine, 7,8-benzoquinoline, 2-chloropyridine, 4-cyanopyridine, and combinations thereof. It is especially preferred to use as catalyst a salt of p-toluenesulfonic acid with pyridine or a salt of p-toluenesulfonic acid with 2,4,6,N,N-pentamethylaniline.

The cations and/or acid ions provided in the catalyst salts to be used pursuant to the invention preferably have alkoxysilyl groups. This causes the catalyst salt to be bound into the polyether matrix after hardening of the dental material, and to be unable any longer to be leached out of the dental impression material.

According to the invention, the dental materials can contain as catalyst b) one or more of the aforementioned salts, or any combination of them with one another. The dental material preferably contains only one of the aforementioned salts as catalyst. It is especially preferred to use no other catalysts besides the one or more salts to be used pursuant to the invention, particularly no organometallic metal salts, tertiary amines, or free acids.

In the dental material pursuant to the invention, it is preferred to use a catalyst salt b) with a pH measured in water (Ampuwa, pH 5.8) between 1 and 7, with special preference between 2 and 6, and most preferably between 2 and 5.

As one skilled in the art knows, the amount of catalyst salt to be used depends in part on the solubility of the salt in the polyether matrix used. The amount of catalyst salt to be used, based on the total dental material mixture, is preferably 0.0005 to 0.5 mmol/g, more preferably 0.0005 to 0.25 mmol/g, and most preferably 0.0005 to 0.05 mmol/g. Of course, the catalyst salt used must have a minimum solubility in the polyether matrix used to be able to act catalytically at all.

To keep the amount of catalyst salt to be used as small as possible, a catalyst salt with sufficiently high solubility in the polyether material, i.e. with adequate catalytic activity, can be used. The catalytic activity is determined as described in connection with the first particular embodiment of this invention.

If the dental material pursuant to the invention is formulated as a single-component material, it should be as absolutely anhydrous as possible to avoid a reaction of the alkoxysilyl-functional and/or hydroxysilyl-functional polyether during storage.

If the dental material is formulated as a two-component system, the catalyst component B preferably contains water c), while the base component A is as absolutely anhydrous as possible. The catalyst component B of the two-component dental material pursuant to the invention preferably contains 0.005 to 3 mmol/g, with particular preference 0.01 to 2 mmol/g, and with greatest preference 0.02 to 1 mmol/g of water c), based on the total mixture.

The dental material pursuant to the invention preferably contains at least one reinforcing filler $e_1$) and/or at least one non-reinforcing filler $e_2$). For formulation as a two-component material, the base component A can contain one of the aforementioned fillers, with at least one reinforcing filler and/or at least one non-reinforcing filler preferably being provided both in the base component A and in the catalyst component B.

Suitable reinforcing fillers $e_1$) in particular are highly dispersed active fillers with a BET surface area of at least 50 $m^2/g$ and/or a primary particle size of less than or equal to 100 nm, with special preference less than or equal to 80 nm. Those with a primary particle size in the nanometer range, which can be present as aggregates and/or agglomerates, are particularly suitable. The at least one reinforcing filler $e_1$) is preferably selected from the group consisting of aluminum hydroxide, zinc oxide, titanium dioxide, zirconium oxide, silicon dioxide, and precipitated and/or pyrogenic silica. Of course the aforementioned compounds can be used individually or in any combination with one another, specifically in either hydrophilic form or with water-repellent treatment.

It is also preferred for the at least one reinforcing filler $e_1$) to be in the form of nanoparticles, as fibrous or flake filler, for example mineral fibrous filler, or as synthetic fibrous filler.

When formulating as two-component materials, it is preferable to provide reinforcing fillers $e_1$) in the base component A that have a maximum water content of 0.5 wt. %, with special preference 0.3 wt. % at the most, with very special preference 0.15 wt. %, and most preferably they are absolutely or essentially anhydrous, with the water content determined by Karl Fischer titration.

According to a particular embodiment of this invention, the at least one reinforcing filler $e_1$) with a BET surface area of greater than 50 $m^2/g$ in the base component A has a pH of 5 to 11, preferably from 5 to 9, and with special preference from 5.5 to 8.5. Degradation of the alkoxysilyl-functional and/or hydroxysilyl-functional polymer during storage is avoided in this way.

When formulating as a two-component system, the base component A, based on component A, preferably contains from 0 to 50 wt. %, more preferably 0.1 to 40 wt. %, and very preferably 0.1 to 30 wt. % of at least one reinforcing filler $e_1$), and the catalyst component B, based on component B, preferably contains 0 to 50 wt. %, more preferably 0.1 to 40 wt. %, and very preferably 0.1 to 30 wt. % of at least one reinforcing filler $e_1$).

Suitable non-reinforcing fillers $e_2$) in principle are the same substances as those for the reinforcing fillers $e_1$), but with the non-reinforcing fillers necessarily having a BET surface area of less than 50 $m^2/g$ (Degussa Silicas, Pigment publication series, Number 12, page 5, and Number 13, page 3). The at least one non-reinforcing filler $e_2$) preferably is a substance selected from the group that consists of alkaline earth metal oxides, alkaline earth metal hydroxides, alkaline earth metal fluoride, alkaline earth metal carbonates, calcium apatite ($Ca_5[(F, Cl, OH, MCO_3)|(PO_4)_3]$, especially calcium hydroxyapatite ($Ca_5[(OH)|(PO_4)_3]$), titanium dioxide, zirconium oxide, aluminum hydroxide, silicon dioxide, precipitated silica, and calcium carbonate. Of course, the aforementioned compounds can be used individually or in any desired combination with one another, specifically either in hydrophilic form or with water-repellent treatment.

The non-reinforcing fillers $e_2$) preferably have an average particle size larger than 0.1 µm (Ullmann's Encyclopedia of Industrial Chemistry, Volume 21, page 523).

In a refinement of the concept of the invention, when formulating the dental material as a two-component system, the at least one non-reinforcing filler $e_2$) in the base component A should have a maximum water content of 0.5 wt. %, with special preference a maximum of 0.1 wt. %, with very special preference a maximum of 0.05 wt. %, and most preferably it is absolutely or essentially anhydrous.

According to a particular embodiment of this invention, the at least one non-reinforcing filler $e_2$) in the base component A has a pH of 5 to 11, preferably from 5 to 9, and with special preference from 5.5 to 8.5, in order to avoid degradation of the alkoxysilyl-functional and/or hydroxysilyl-functional polyether during storage.

The base component A of the dental material pursuant to the invention, based on the component A, preferably contains 0 to 80 wt. %, with special preference 0.05 to 75 wt. %, and most preferably 0.1 to 70 wt. % of at least one non-reinforcing filler $e_2$), and the catalyst component B, based on the component B, preferably contains 0 to 80 wt. %, with special preference 0.05 to 75 wt. %, and most preferably 0.1 to 70 wt. % of at least one non-reinforcing filler $e_2$).

In a refinement of the concept of the invention, it is proposed when formulating as a two-component material, that the reinforcing and/or non-reinforcing filler contained in the catalyst component B have a pH between 6.0 and 11.0, and very especially preferred is one with a pH between 7.0 and 10.0.

The total overall content of fillers when formulating the dental materials either as a one-component system or as a two-component system, based on the total mixture, amounts to 0 to 80 wt. %, preferably 0.01 to 80 wt. %, with special preference 0.1 to 75 wt. %, and most preferably 0.2 to 70 wt. %.

In furtherance of the concept of the invention, it is proposed that one or more of the following additives and/or auxiliaries be added to the dental material pursuant to the invention:
f) Thixotropic agent,
g) Water scavenger,
h) Paste-former,
i) Surfactant,
j) Active ingredient,
k) Plasticizer,
l) Optical scanning facilitator,
m) Flavor and/or odorant,
n) Diagnosis facilitator,
o) Fluoridation agent,
p) Bleach,
q) Desensitizing agent,
r) Bonding agent,
s) Colorant,
t) Indicator
u) Stabilizer (antioxidant, free radical scavenger)

Thixotropic agents f) can optionally be added to the dental material pursuant to the invention, for which high molecular weight polyethers such as polyethylene glycol, polyethylene glycol/polypropylene glycol copolymers, polytetrahydrofuran, hydrocarbon waxes, amide waxes, triglycerides, silicas, and silicates have proved to be particularly suitable.

According to a particular embodiment of this invention, the dental materials, when formulated as a two-component system, in the base component A preferably have at least one water scavenger g), which is selected with special preference from the group that consists of alkoxysilanes, titanates such as tetraisopropyl titanate, zirconates such as tetrapropyl zirconate, zeolites, aluminum sulfate, anhydrous calcium sulfate (e.g. Drierite®), Blue Gel, and/or oxazolidines.

In a refinement of the concept of the invention, it is proposed to use as water scavenger g) one or more functional alkoxysilanes, since the speed of crosslinking, the structure, and the properties of the resultant elastomer can be adjusted additionally by such compounds. It is preferred for the at least one functional alkoxysilane to be a compound with the general formula V $$R^8{}_{4-x}\text{—Si—}R^9{}_x$$

wherein $R^8$=H, alkyl, alkenyl, —$(CH_2)_n$-Z, with n=1 to 6, $R^9$=Alkoxy,
Z=$NH_2$, NHR, $NR_2$, with R=Alkyl, aminoalkyl, —C(O)$OCH_3$, and
x=1, 2, 3, or 4,
wherein it is especially preferred if $R^8$=alkenyl, especially vinyl, or —$(CH_2)_n$-Z, with Z=NHR and n=1 or 3, especially n=1, and/or x=3 and/or R=—C(O)$OCH_3$.

It is particularly preferred for the at least one functional alkoxysilane g) to be vinyltrimethoxysilane, N-trimethoxysilylmethyl-O-methylcarbamate and/or a compound with the following formula:

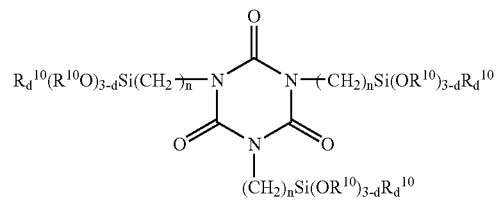

wherein n=1 to 6, preferably n=1 or 3, with special preference n=1, d=0 or 1, and
$R^{10}$=a linear or branched $C_1$-$C_{30}$ alkyl group in which the hydrogen atoms may be partially substituted by halogen atoms, OH—, $NH_2$—, $NO_2$—, or other $C_1$-$C_6$ alkyl groups.

The aforementioned compounds are reactive silanes that function as water scavengers to eliminate traces of water still present in component A of the dental composition.

Specifically when it is formulated as a two-component system, the two-component dental material pursuant to the invention preferably also contains in the catalyst component B at least one paste-former h), since this permits setting a paste-like consistency, for example free-flowing, semifluid, or high-viscosity, and makes possible a homogeneous blending of the salt and the solid reinforcing and non-reinforcing fillers. Preferably used as at least one paste-former h) is a compound selected from the group that consists of polyethers, polyvinylpyrrolidones, polyurethanes, polyesters, waxes, vaseline, paraffin oils, silicone oils, polyfunctional alcohols, propylene glycol, polypropylene glycols, ethylene glycols, polyethylene glycols, copolymers of N-vinylpyrrolidone and vinyl acetate, carboxymethyl-, methyl-, hydroxyethyl-, hydroxypropylcellulose, polysaccharides, glycerin, and poly(meth)acrylic acids. Of course, the dental materials pursuant to the invention may also contain any combination of two or more of the aforementioned compounds.

Hydrophilic paste-formers in which the catalyst base can be mixed homogeneously with water are especially preferred. The miscibility can be improved further by adding surfactants. Particularly preferred representatives are polyethers, polyurethanes, polyesters, polyfunctional alcohols, especially propylene glycols, polypropylene glycols, ethylene glycols, polyethylene glycols, butylene glycols, polybutylene glycols, and glycerin, as well as their mixtures and copolymers.

The compounds i) optionally used as surfactant, emulsifier, and/or stabilizer are preferably anionic surfactants, with special preference alkyl sulfates, alkylbenzenesulfonates, or alkylbenzenephosphates, cationic surfactants, with special preference tetraalkylammonium halides, nonionic surfactants, with special preference alkyl- and alkylphenyl polyalkylalkylene oxides, fatty acid alkoxylates, fatty alcohol alkoxylates and their alkyl ethers and alkyl esters, fatty acid alkylolamides, sucrose fatty acid esters, trialkylamine oxides, silicone surfactants (e.g. Silwet L77, Tegopren 5878, Masil SF19), or fluoro surfactants, or amphoteric surfactants, with special preference sulfated or ethoxylated condensation products of alkenylphenols and formaldehyde, ethylene oxide/propylene oxide block polymers, or modified polysiloxanes. Surfactants that can be copolymerized into the alkoxysilyl-functional and/or hydroxysilyl-functional polyethers a), such as those disclosed in U.S. Pat. No. 4,160,778, the disclosure of which is herein incorporated by reference, can also be used advantageously. In addition or alternatively thereto, derivatives of the aforementioned surfactants can also be used, for example those that have functional groups such as —OH, —CH=CH$_2$, —OCO—(CH$_3$)C=CH$_2$, and alkoxysilyl groups. Also, other surfactants known to one skilled in the art can be used, although less preferably.

It is preferred to use a silicone surfactant as the used compound i), since it has been found surprisingly in the course of this invention that very low contact angles can be produced in the polyether matrix with these compounds, as determined by the "sessile drop" method.

These mixtures are distinguished by excellent wettability and outstanding flow properties onto wet dental and tissue substance. Despite these good hydrophilic properties, the material does not swell in contact with aqueous media such as water, saliva, blood, disinfectant bath, or aqueous plaster slurry. The good initial wettability of the mixtures is important for the accurately detailed impression from the impression material in the patient's mouth during processing and in the first contact with wet oral/dental substance, and is manifested by a low contact angle of less than 50°, in particular less than or equal to 45°, measured with a contact angle measuring instrument from the Kruss Company at 20° C. by the "sessile drop" method. In addition, the hardened impression at the time of filling with plaster (immediately or 2 hours after hardening) is distinguished by a contact angle smaller than 60°, in particular less than or equal to 55°.

Also, the dental materials pursuant to the invention may contain one or more active ingredients j), that may be present in the base component A or the catalyst component B, depending on their chemical functionality when formulated as a two-component system. Among the active ingredients to be used pursuant to the invention in particular are astringents such as epinephrine, substances with antibacterial and/or antifungal activity such as hexitidine (e.g. 5-amino-1,3-bis(2-ethylhexyl)-5-methylhexahydropyrimidine), triclosan (e.g. 2,4,4'-trichloro-2-hydroxydiphenyl ether), and chlorhexidine:

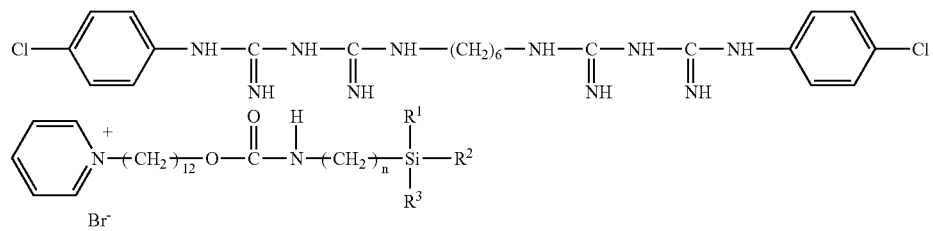

wherein R$^1$, R$^2$, and R$^3$ independently of one another are alkoxy, alkyl, aryl, aralkyl, alkylaryl groups, or hydrogen, preferably butoxy, propoxy, ethoxy, methoxy, hexyl, pentyl, butyl, propyl, ethyl, or methyl groups, with particular preference ethoxy, methoxy, ethyl, or methyl groups, provided that at least one of the aforementioned groups, preferably two or all three groups, are alkoxy groups.

Useful plasticizers k) in particular are unreactive polyethers, polydialkylsiloxanes, silicone oils, polyesters, polyurethanes, phthalates, mono-, di-, tri-, or higher-functional esters, particularly acetyl(tributyl citrate), Mesamoll® (Bayer), and triglycerides, which are added to component A and/or to component B depending on their chemical nature, when formulating as a two-component system.

As compounds l) that enable optical reading/scanning by means of a scanner and/or intraoral camera (Cerec®, Sirona Co.), all substances known to one skilled in the art for this purpose, particularly metal powders, metal pigments, metallic pigments, zinc oxide, zirconium oxide, and titanium dioxide, can be added to component A and/or to component B, depending on their chemical nature, when formulating as a two-component system.

In addition, the dental materials pursuant to the invention can contain in one of the two components, or in both of them, the usual flavors and/or odorants m) and/or the additives n) useful for diagnostics, as described, for example, in European Patent No. EP 1 339 373, International Application No. PCT/EP00/05418, German Patent No. DE 35 02 594, and German Patent No. DE 100 61 195.

Fluoridation agents that have proved particularly suitable are sodium fluoride, potassium fluoride, ammonium fluoride, fluorophosphates, and amine fluorides such as N'-octadecyl-bimethylenediamine-N,N,N'-bis(2-ethanol) dihydrofluoride (as described in ZM 93, Number 15, pages 32 ff.). They can be added to component A and/or to component B when formulating as a two-component system, likewise depending on their chemical nature.

The dental material pursuant to the invention when formulated as a two-component system can also contain one or more different peroxides in component A and/or component B as bleaches p), which are preferably selected from the group that consists of alkali metal and alkaline earth metal peroxides, hydrogen peroxide, and carbamide peroxide.

Examples of suitable desensitizing agents q) are potassium salts such as potassium nitrate, oil of cloves, and eugenol.

Alkoxysilanes, epoxysilanes, aminosilanes, and methacrylate silanes are especially suitable as bonding agents r), for example to develop an adhesive bond between the impression material and a stainless steel or plastic impression mold.

Examples of suitable colorants s) are dyestuff pigments in the form of Al, Ca, Ba oxides/laked colorant, which like the previously described auxiliary substances, if not otherwise indicated, can be added to component A and/or to component B when formulating as a two-component system, depending on their chemical nature.

When formulating as a two-component system, dye indicators t) can also be added to the dental material pursuant to the invention in component A and/or in component B that change color as a function of pH, for example because of pH changes when mixing components A and B, or upon contact with water.

Compounds can be added to the two-component dental materials pursuant to the invention as stabilizers and/or antioxidants u), in particular those selected from the group consisting of polymeric trimethyldihydroquinoline, diphenyl derivatives, phenothiazine, phenyl-α-naphthylamine, 4,4'-methylenebis(2,6-di-tert-butylphenol), butylhydroxytoluene, butylhydroxyanisole (BHA), and methoxyphenol (hydroxyanisole). Examples of such compounds are the products commercially available from the Ciba-Geigy Company Irganox® 1010, 1076, 1035, MD 1024, Irgafos 168, 38, Irgacor 252 LD/252FC, 1405, 1930, 153, Tinuvin® 328, P, 384, 900, 928, 327, 1130, 400, 292, 144, 123, 622, and Chimassorb® 119.

The two-component dental material pursuant to the invention is preferably packed and proportioned properly for later use in suitable primary packages such as tubes, cans, and with special preference in cartridges and foil bags such as those described in European Patent No. EP 0 723 807 A2, European Patent No. EP-A-0 541 972, International Application No. PCT/EP/980193, European Patent No. EP-A-0 492 412, European Patent No. EP-A-0 492 413, and European Patent No. EP 0 956 908 A1, the disclosures of all of which are hereby incorporated by reference.

Another object of this invention is mixtures that are obtainable by blending components A and B of the previously described two-component dental material pursuant to the invention. The base component A is preferably blended with the catalyst component B in a ratio of 1:1 to 20:1, with special preference from 1:1 to 10:1, and most preferably a ratio of 1:1, 2:1, 4:1, or 5:1.

DETAILED DESCRIPTION OF THE PREFERRED EMBODIMENTS

The invention will be explained below with reference to examples that demonstrate the concept of the invention but do not limit it.

Example 1

Pursuant to the Invention (Preparation of a dimensionally stable vulcanizate/cast of a dental impression material based on alkoxysilyl-functional and/or hydroxysilyl-functional polyethers by adding ethylenediaminetetraacetic acid as acidic compound d) to the base component A)

Preparation of Catalyst Component B 2.80 parts of a salt of 1,9-diazabicyclo[5.4.0]undec-7-ene and 2-ethylhexanoic acid was dissolved in 5 parts of deionized water (Ampuwa, pH 5.8). The salt solution was mixed in a vacuum mixing flask with 36 parts of polypropylene glycol with a molecular weight of 4,000 g/mole, 51 parts of aluminum hydroxide with an average particle size of 13 μm and a BET surface area of 1 $m^2$/g, and 5 parts of a silica gel with a BET surface area of 130 $m^2$/g, for 5 minutes. The mixture was then homogenized by mixing for 30 minutes longer under vacuum.

A semifluid material (ISO 4823) was obtained that represents the catalyst component B of the impression material pursuant to the invention based on alkoxysilyl polyethers. The material was loaded into foil bags (PE/Al/PE laminated film) and stored.

Preparation of Base Component A 39 parts of a polypropylene glycol that was terminally functionalized with dimethoxymethylsilyl groups through urethane groups and methylene spacers, with the polypropylene glycol having a viscosity of 10,000 mPa·s at 20° C., was mixed in a vacuum mixer under a dry argon protective atmosphere with 51 parts of a dried cristobalite filler surface-modified with trimethylsilyl groups with an average particle size of 7 μm, two parts of a dried, micronized pyrogenically produced silica rendered water-repellent, with a BET surface area of 170 $m^2$/g, 0.4 part of vinyltrimethoxysilane and 0.4 part of N-trimethoxysilylmethyl-O-methylcarbamate, two parts of silicone surfactant, and 0.8 part of ethylenediaminetetraacetic acid, for 5 minutes. Mixing was continued for 30 minutes longer under vacuum until homogeneous.

A semifluid material (ISO 4823) was obtained that represents the base component A of the impression material pursuant to the invention based on alkoxysilylpolyethers. The material was loaded into foil bags (PE/Al/PE laminated film) and stored.

Mixture of Catalyst Component B and Base Component A

One part of the previously described catalyst component B and 5 parts of the base component A prepared according to the above instructions were mixed homogeneously in each case and hardened, using an electric dispenser for foil bags (Plug & Press System, Kettenbach GmbH & Co. KG) through a dynamic mixer (Kettenbach GmbH & Co. KG).

The hardened vulcanizate had the following properties in use:

| | |
|---|---|
| Shore A hardness: | immediately after setting: 52<br>after 24 h: 61 |
| Recovery after deformation: | 98.6% |
| Consistency of catalyst component B: | 38 mm |
| Consistency of base component A: | 36 mm |
| Consistency of mixture | 35 mm |
| Linear dimensional change: | −0.42% |
| Contact angle 45 sec after beginning to mix: | 40° |
| Processing time: | 2:00" |
| Setting time: | 6:00" |
| Deformation 1: | 0.00 mm |

To test dimensional stability in the sense of the invention, rectangular test specimens of the hardened dental impression material from components A and B with dimensions of 40×12.5×5 mm and a Shore A hardness of 52 (immediately after complete setting) were fastened by one end to a slide so that one half, 20×12.5,×5 mm, extends unsupported beyond the slide, and is exposed to the gravitational force of its own weight.

The supported and unsupported areas of the test specimen were chosen so that no spontaneous deformation occurs from the force of gravity alone. Supporting on half of the test specimen surface as indicated here, or 20×12.5×5 mm, proved practical for test specimens with a Shore A hardness of 50 to 70. Other test specimens with a Shore A hardness of 30-50 should be applied with a larger support surface of 70%, or 28×12.5×5 mm, and correspondingly smaller unsupported surface of 30%, or 12×12.5×5 mm. At given time intervals, the vertical deflection 1 (deformation) of the test specimen was measured relative to its original starting position.

As shown by the aforementioned technical data for the hardened vulcanizate, the materials pursuant to the invention satisfy all the requirements for a functional dental impression material. In particular, the hydrophilicity as determined by contact angle measurements shows outstanding values. The material obtained in this example is also distinguished by the fact that the vulcanizates/casts obtained are dimensionally stable even after storage for 2 weeks at 60° C. and/or for 3 months at room temperature.

Surprisingly, the storage stability of the base component is not impaired by the addition of ethylenediaminetetraacetic acid, in other words neither premature crosslinking nor viscosity increase occurs during the time of storage.

The ethylenediaminetetraacetic acid used in Example 1 has a water solubility of 0.5 g/l at 20° C. and is thus within the range pursuant to the invention. Also, ethylenediaminetetraacetic acid has the following $pK_a$ values in water: $pK_{a1}$=2.0, $pK_{a2}$=2.67. and $pK_{a3}$=6.16. These three $pK_a$ values are within the range of $pK_a$ values of 1 to 6.5 preferred pursuant to the invention. In addition to this, the polyether solubility of less than or equal to 2 g/l or less than or equal to 0.5 g/l is within the range preferred pursuant to the invention.

The applied characteristics of the material obtained in Example 1 are summarized in Table 1. The effect of the acidic compound used pursuant to the invention on the setting time measured by recovery after deformation compared to that of commercial products of the state of the art is also shown in Table 2. It is apparent from Table 2 that the addition of an acidic compound surprisingly exerts no negative influence on the setting time.

Example 2

Pursuant to the Invention (Preparation of a Dimensionally Stable Vulcanizate/Cast of a Dental Impression Material Based on Alkoxysilyl-Functional and/or Hydroxysilyl-Functional Polyethers by Adding Ethylenediaminetetraacetic Acid to the Base Component A) as Acidic Compound d)

The procedure analogous to Example 1 was followed, with the amount of ethylenediaminetetraacetic acid being reduced to 0.56 part.

The vulcanizates/casts obtained were dimensionally stable after storage for two weeks at 60° C. or for 3 months at room temperature.

Surprisingly, the storage stability of the base component A is not impaired by the addition of ethylenediaminetetraacetic acid, in other words neither premature crosslinking nor viscosity increase occurs during the time of storage.

The applied characteristics of the material obtained in Example 2 are summarized in Table 1. The effect of the acidic compound used pursuant to the invention on the setting time measured by recovery after deformation compared to that of commercial products of the state of the art is also shown in Table 2. It is apparent from Table 2 that the addition of an acidic compound surprisingly exerts no negative influence on the setting time.

Example 3

Pursuant to the Invention (Preparation of a Dimensionally Stable Vulcanizate/Cast of a Dental Impression Material Based on Alkoxysilyl-Functional and/or Hydroxysilyl-Functional Polyethers by Adding Barbituric Acid to the Base Component A) as Acidic Compound d)

Preparation of Catalyst Component B

The catalyst component from Example 1 was used as catalyst component B.

Preparation of Base Component A

The base component from Example 1 was used as base component A, with 0.28 part of barbituric acid having been used instead of ethylenediaminetetraacetic acid.

Mixture of Catalyst Component B and Base Component A

One part of the previously described catalyst component B and 5 parts of the base component A prepared according to the above instructions were mixed homogeneously in each case and hardened, using an electric dispenser for foil bags (Plug & Press System, Kettenbach GmbH & Co. KG) through a dynamic mixer (Kettenbach GmbH & Co. KG).

Dimensional stability was tested analogously to the method of Example 1.

It was found that the vulcanizates/casts obtained were dimensionally stable even after storage for one week at 60° C. or for one month at room temperature.

Surprisingly, the storage stability of the base component A is not impaired by the addition of barbituric acid, in other words neither premature crosslinking nor viscosity increase occurs during the time of storage.

The barbituric acid used in Example 3 has a water solubility of 142 g/l at 20° C. and thus lies within the range pursuant to the invention. In addition, it has a $pK_a$ value of 4.01 in water that lies within the $pK_a$ range preferred pursuant to the invention of 1 to 6.5. The polyether solubility of less than or equal to 2 g/l likewise is within the range preferred pursuant to the invention.

The applied properties of the material obtained in Example 3 are summarized in Table 1.

Example 4

Pursuant to the Invention (Preparation of a Dimensionally Stable Vulcanizate/Cast of a Dental Impression Material Based on Alkoxysilyl-Functional and/or Hydroxysilyl-Functional Polyethers by Adding Succinic Anhydride to the Base Component A) as Acidic Compound d)

Preparation of Catalyst Component B

The catalyst component from Example 1 was used as catalyst component B.

Preparation of Base Component A

The base component from Example 1 was used as base component A, with 0.11 part of succinic anhydride having been used instead of ethylenediaminetetraacetic acid.

Mixture of Catalyst Component B and Base Component A

One part of the previously described catalyst component B and 5 parts of the base component A prepared according to the above instructions were mixed homogeneously in each case and hardened, using an electric dispenser for foil bags (Plug & Press System, Kettenbach GmbH & Co. KG) through a dynamic mixer (Kettenbach GmbH & Co. KG).

Dimensional stability was tested analogously to the method of Example 1.

It was found that the vulcanizates/casts obtained were dimensionally stable even after storage for one week at 60° C. or for one month at room temperature.

Surprisingly, the storage stability of the base component A is not impaired by the addition of succinic anhydride, in other words neither premature crosslinking nor viscosity increase occurs during the time of storage.

The succinic anhydride used in Example 4 is opened after the mixing process by the water from catalyst component B to form succinic acid, which has a $pK_a$ of 4.19, within the range of $pK_a$ values of 1 to 6.5 preferred pursuant to the invention.

The applied properties of the material obtained in Example 4 are summarized in Table 1.

Comparison Example 1

(Preparation of a Vulcanizate/Cast of a Dental Impression Material Based on Alkoxysilyl-Functional and/or Hydroxysilyl-Functional Polyethers without the Addition of an Acidic Compound d) to the Base Component A)

Preparation of Catalyst Component B

The catalyst component from Example 1 was used as catalyst component B.

Preparation of Base Component A

The base component from Example 1 was used as base component A, without the addition of form-stabilizing ethylenediaminetetraacetic acid.

Mixture of Catalyst Component B and Base Component A

One part of the previously described catalyst component B and 5 parts of the base component A prepared according to the above instructions were mixed homogeneously in each case and hardened, using an electric dispenser for foil bags (Plug & Press System, Kettenbach GmbH & Co. KG) through a dynamic mixer (Kettenbach GmbH & Co. KG).

The technical data with regard to Shore A hardness for the hardened impression material obtained in Comparison Example 1 immediately after it had set completely (52) corresponded to that of the material obtained in Example 1.

The dimensional stability was tested in the same way as in Example 1.

The vulcanizates/casts obtained after hardening deformed (even partially melted) after only 10 days of storage at 60° C. or after storage at room temperature for 4 weeks, by more than 0.5 mm. A corresponding dental impression becomes unusable after this storage since deformed or melted impressions distort the tooth pattern and would lead to unusable dentures. For this reason alone, the material obtained in Comparison Example 1 is unsuitable as dental impression material.

The applied properties of the material obtained in Comparison Example 1 are summarized in Table 1.

Comparison Example 2

(Attempts to Prepare Vulcanizates/Casts of a Dental Impression Material Based on Alkoxysilyl-Functional and/or Hydroxysilyl-Functional Polyethers with the Addition of p-Toluenesulfonic Acid to the Base Component A)

Preparation of Catalyst Component B

The catalyst component from Example 1 was used as catalyst component B.

Preparation of Base Component A

The base component from Example 1 was used as base component A, with the 0.8 part of ethylenediaminetetraacetic acid being replaced by 0.52 part of p-toluenesulfonic acid.

The mixture began to crosslink even while the p-toluenesulfonic acid was being mixed in. The material had completely hardened a few minutes after adding the acid.

This example shows impressively that not every acidic compound is suitable for producing dimensionally stable vulcanizates/casts. The p-toluenesulfonic acid used in this example has a water solubility of about 750 g/l, outside of the range of water solubility (20° C.) pursuant to the invention. In addition, the $pK_a$ value of 0.7 in water is very low and outside of the range of 1.0 to 6.5 preferred pursuant to the invention. Furthermore, the polyether solubility of p-toluenesulfonic acid is relatively high. Premature crosslinking of the alkoxysilyl- and/or hydroxysilylpolyether occurs with this material even in the preparation phase particularly because of its high water solubility. Therefore, it is no more possible to prepare a storable dental impression material than it is to produce test specimens to test dimensional stability.

The applied properties of the material obtained in Comparison Example 2 are summarized in Table 1.

Comparison Example 3

(Attempts to Prepare Vulcanizates/Casts of a Dental Impression Material Based on Alkoxysilyl-Functional and/or Hydroxysilyl-Functional Polyethers with the Addition of Phosphoric Acid to the Base Component A)

Preparation of Catalyst Component B

The catalyst component from Comparison Example 1 was used as catalyst component B.

Preparation of Base Component A

The base component from Example 1 pursuant to the invention was used as base component A, with the 0.8 part of ethylenediaminetetraacetic acid being replaced by 0.27 part of 30% phosphoric acid.

The mixture began to crosslink even while the phosphoric acid was being mixed in. The material had completely hardened only a few minutes after adding the acid. It is no more possible to prepare a storable dental impression material with this material than it is to produce test specimens to test dimensional stability.

This Comparison Example also shows that not every acidic agent is suitable for making dimensionally stable vulcanizates/casts. The water solubility of 750 g/l of the phosphoric acid used in this example is likewise far outside of the range of water solubility intended by the invention.

The applied properties of the material obtained in Comparison Example 1 are summarized in Table 1.

TABLE 1

Dimensional stability and effect on storage stability of base component A of acidic compounds in base- and/or salt-catalyzed condensation-crosslinking two-component dental impression materials based on alkoxysilyl-functional polyethers

| Example/ Comparison Example | Acidic Compound | Concentration [%] | Storage stability[1]) of base component A | Setting behavior after mixing components A + B | Dimensional stability of hardened vulcanizate | Deformation I[4]) 10 days 60° C. |
|---|---|---|---|---|---|---|
| Example 1 | Ethylenediamine-tetraacetic acid CAS No. 60-00-4 | 0.8 | Storage stability: no viscosity increase no hardening | no acceleration no inhibition | No deformation Dimensionally stable | 0.00 mm |
| Example 2 | Ethylenediamine-tetraacetic acid | 0.56 | Storage stability: no viscosity increase no hardening | no acceleration no inhibition | No deformation Dimensionally stable | 0.00 mm |
| Example 3 | Barbituric acid | 0.28 | Storage stability: slight viscosity increase no hardening | no acceleration slight inhibition | Very slight deformation Dimensionally stable | 0.05 mm |
| Example 4 | Succinic anhydride | 0.11 | Storage stability: slight viscosity increase no hardening | no acceleration slight inhibition | Slight deformation Dimensionally stable | 0.1 mm |
| Comparison Example 1 | No additive | 0 | Storage stability: no viscosity increase no hardening | no acceleration no inhibition | Not dimensionally stable | 0.58 mm |
| Comparison Example 2 | p-Toluene-sulfonic acid | 0.52 | Crosslinks immediately after addition | not possible[2]) | not possible[2]) | |
| Comparison Example 3 | Phosphoric acid | 0.27 | Crosslinks immediately after addition | not possible[2]) | not possible[2]) | |

| Example/ Comparison Example | Elastic recovery after deformation | | | Shore A hardness | | | Suitability |
|---|---|---|---|---|---|---|---|
| | AM[5]) | 1W[6]) 60° C. | 2W[6]) 60° C. | AM[5]) | 1W[6]) 60° C. | 2W[6]) 60° C. | |
| Example 1 | 98.6 | 99.9 | 99.9 | 68 | 70 | 70 | +++ |
| Example 2 | 98.7 | 99.9 | 99.9 | 68 | 70 | 70 | +++ |
| Example 3 | 98.5 | 99.9 | 99.9 | 68 | 70 | 70 | ++ |
| Example 4 | 98.2 | 99.8 | 99.8 | 68 | 70 | 70 | + |
| Comparison Example 1 | 99.3 | 99.9 | —[3]) | 69 | 66 | 61 | --- |
| Comparison Example 2 | — | | | | | | --- |
| Comparison Example 3 | — | | | | | | --- |

--- unsuitable
+++ very well suited
--- unsuitable
+++ very well suited
[1])Storage at room temperature and at 60° C. (1 week, 2 weeks, 3 weeks, 4 weeks)
[2])material crosslinks immediately after addition of the acid compound in base component A mixing of component A with component B was therefore not possible.
[3])Not measurable since test specimen melted
[5])Initial measurement
[6])1 to 2 weeks storage time

TABLE 2

Setting time determination by recovery after deformation following ISO 4823 (1992 Version)

| | Aziridinopolyether 1 Base LOT 166056 Cat LOT 166145 | Aziridinopolyether 2 Base LOT 174886 Cat LOT 174697 | Alkoxysilylpolyether 1 Base LOT 200047 Cat LOT 195039 | A-Silicone Base LOT 0409000261 Cat LOT 0409000261 |
|---|---|---|---|---|
| Package insert data | Full setting: 6'00" | Full setting: 6'00" | Full setting: at least 5'15" | Full setting: at least 5'15" |
| Recovery after deformation after | | | | |
| 6'00" | 98.15% | 98.70% | 98.30% | 98.40% |
| 5'00" | 97.50% | 97.40% | 98.00% | 98.00% |

TABLE 2-continued

Setting time determination by recovery after deformation following ISO 4823 (1992 Version)

| | | | | |
|---|---|---|---|---|
| 4'00" | 96.40% | 96.30% | 97.10% | 97.90% |
| 98.00%[1),2),3)] reached by: | 5'45" | 5'30" | 5'00" | 5'00" |

| | Alkoxysilylpolyether Example 2 pursuant to the invention 0.56% ethylenediamine-tetraacetic acid | Alkoxysilylpolyether Example 1 pursuant to the invention 0.8% ethylenediamine-tetraacetic acid | Alkoxysilylpolyether Comparison Example 1 not pursuant to the invention with no ethylenediamine-tetraacetic acid |
|---|---|---|---|
| Package insert data Recovery after deformation after | — | — | — |
| 6'00" | 98.70% | 98.60% | 98.90% |
| 5'00" | 98.20% | 98.00% | 98.10% |
| 4'00" | 95.90% | 96.80% | 94.80% |
| 98.00%[1),2),3)] reached by: | 5'00" | 5'15" | 5'00" |

Aziridinopolyether 1: Impregum penta (ESPE)
Aziridinopolyether 2: Impregum penta soft (ESPE)
Alkoxysilylpolyether 1: P2 Magnum 360 Monophase (Heraeus Kulzer)
A-Silicone: Aquasil ultra Monophase (Dentsply)
[1)]Calculated by interpolation
[2)]The value of 98.00% was chosen as a reasonable standard value at which a qualitatively high-grade precision impression can be taken
[3)]The full setting time is rounded off by ±15 seconds; determination was carried out by measurement of recovery after deformation according to ISO 4823 (1992 Version)

What is claimed is:

1. A condensation-crosslinkable dental material comprising component A and component B, wherein said component A comprises:
   a) at least one alkoxysilyl-functional and/or hydroxysilyl-functional polyether and
   d) at least one acidic compound that has a water solubility at 20° C. of no more than 150 g/l; and
wherein said component B comprises:
   b) at least one catalyst selected from the group consisting of bases, salts, and combinations thereof, and
   c) optionally water.

2. A dental material according to claim 1, wherein said at least one acidic compound d) is selected from the group consisting of organic acids, inorganic acids, inorganic acid anhydrides, organic acid anhydrides, and combinations thereof.

3. A dental material according to claim 1, wherein said at least one acidic compound d) has a water solubility (20° C.) of no more than 50 g/l.

4. A dental material pursuant to claim 1, wherein the at least one acidic compound d) has a $pK_a$ value measured in water (20° C.) between 1.0 and 6.5.

5. A dental material pursuant to claim 1, wherein the dental material, based on the total mixture, contains 0.001 to 10 wt. %, of the at least one acidic compound d).

6. A dental material pursuant to claim 1, wherein the dental material is formulated so that after hardening and subsequent storage for 1 week at 60° C., or after hardening and subsequent storage for 12 weeks at room temperature, it has a deformation of less than 1 mm.

7. A dental material pursuant to claim 1, wherein the component A is stable in storage at room temperature for at least 6 months, or at a storage temperature between 40° C. and 60° C. for at least 1 week.

8. A dental material according to claim 1, wherein said at least one catalyst b) is an organic base with a $pK_{BH+}$ measured in acetonitrile of at least 20.

9. A dental material according to claim 8, wherein the material contains 0.001 to 1 mmol/g of catalyst b) based on the total mixture.

10. A dental material according to claim 1, catalyst b) is formed from at least one salt formed from a cation and an anion, the cation being selected from the group consisting of
   complexes of alkali metal or ammonium cations with crown ethers and/or cryptands,
   tetraalkyl-, tetraaryl- trialkylaryl-, dialkyldiaryl-, monoalkyltriarylammonium cations, tetraalkyl-, tetraaryl-, trialkylaryl-, dialkyldiaryl-, monoalkyltriarylphosphonium cations, tetraalkyl-, tetraaryl- trialkylaryl-, dialkyldiaryl-, monoalkyltriarylarsonium cations, tetraalkyl-, tetraaryl- trialkylaryl-, dialkyldiaryl-, monoalkyltriarylstibonium cations,
   cations formed by protonation of a base with a $pK_{BH+}$ value of at least 20 measured in acetonitrile
   and combinations thereof, and
   said anion being a saturated or unsaturated (cyclo)aliphatic carboxylic acid, with the carboxylic acid being a branched carboxylic acid with a (cyclo)alkyl chain provided on the carboxyl group of at least 2 carbon atoms, or an unbranched carboxylic acid with a (cyclo)alkyl chain provided on the carboxyl group, said chain having a length of at least 4 carbon atoms.

11. A dental material according to claim 10, wherein the anion of the at least one catalyst b) is an anion of a branched carboxylic acid with the (cyclo)alkyl chain on the carboxyl group having a length of at least 3 carbon atoms, or an unbranched carboxylic acid with a (cyclo)alkyl chain on the carboxyl group having a length of at least 5 carbon atoms.

12. A dental material according to claim 1, wherein the at least one catalyst b) comprises at least one salt that is formed from a weak organic base with a $pK_{BH+}$ measured in water between −1 and 7 and at least one strong acid with a $pK_a$ value measured in water of less than 2.

13. A dental material according to claim 12, wherein the strong acid has a structure that allows mesomeric stabilization of a negative charge after deprotonation of the acid.

14. A dental material pursuant to claim 12, wherein the at least one base has a $pK_{BH+}$ measured in water between 1 and 7 and the at least one strong acid has a $pK_a$ measured in water of less than 1.

* * * * *